United States Patent
Campbell et al.

(10) Patent No.: US 6,177,419 B1
(45) Date of Patent: Jan. 23, 2001

(54) BIPYRIDINE MANGANESE COMPLEXES

(75) Inventors: Ian Baxter Campbell, Broom; Ann Louise Walker, Wood Green; Philip Charles Box, Ware; Gerard Martin Paul Giblin, Shefford; George Edward Tranter, Kidlington, all of (GB)

(73) Assignee: Eukarion, Inc., Bedford, MA (US)

( * ) Notice: Under 35 U.S.C. 154(b), the term of this patent shall be extended for 0 days.

(21) Appl. No.: 09/376,044

(22) Filed: Aug. 17, 1999

(30) Foreign Application Priority Data

Aug. 17, 1998 (GB) .................................... 9817845

(51) Int. Cl.[7] ........................ A61K 31/33; C07D 213/04; C07D 225/00
(52) U.S. Cl. ........................... 514/183; 546/255; 540/465
(58) Field of Search .................... 546/257, 255; 514/334, 183; 540/465

(56) References Cited

FOREIGN PATENT DOCUMENTS

WO 94/27949  12/1994 (WO).
WO 97/32853   9/1997 (WO).

OTHER PUBLICATIONS

Capdevielle, P., et. al., New J. Chem., Electroactive Polymers exchanging Transition Metal Ions; Synthesis of New Monomers and Polymers Based on 6, 6'–bis(2–hydroxyphenyl) bipyridine Complexes, 1994*
Wolfbauer, G. et. al., J. Am. Chem. Soc., Experimental and Theoretical Investigations of the Effect of Deprotonation on Electronic Spectra and Reversible Potentials of Photovoltaic Sensitizers: Deprotonation of cis–L2RuX2 (L=2,2'–Bipyridine–4,4'–dicarbo, 2000.*
Benaglia, M., et al., "Synthesis of Pyridylstannanes from Halopyridines and Hexamethyldistannane with Catalytic Palladium," *Tetrahedron Lett.*, 38:4737–4740 (1997).
Uenishi, J., et al., "Ipso Substitution of 2–Alkysulfinylpyridine by 2–Pyridyllithium; A New Preparation of Oligopyridine and Their Bromomethyl Derivatives," *Tetrahedron Lett.*, 31:4625–4628 (1990).
Constable, E.C., "A Novel Rearrangement of 2, 2'–Bipyridine N,N'–Dioxides. The Characterisation of Dipyrido [1,2–b:2,3–d] Isoxazolinium Salts as Intermediates in the Formation of 3–Hydroxy–2,2'–Bipyridines," *Tetrahedron* 39:291–295 (1983).
Neumann, U. et al., "4,4'–Donor–substituierte und 6,6'–difunktionalisierte 2,2'–Bipyridine," *Chem. Ber.* 122:589–591 (1989).
Uchida, Y. et al., "Reactions of Heteroaryllithium Compounds with Phosphorus Trichloride, Phosphorus Oxychloride, and Thionyl Chloride. Formation of Heterocyclic Biaryls," *Heteroatom Chemistry*, 5 (4) :409–413 (1994).
Audebert, P. et al., "Electrochemical Polymerization of Several Salen–Type Complexes. Kinetic Studies in the Microsecond Time Range," *Journal of Electroanalytical Chemistry*, 338 (1–2) :269–278 (1992).
Rodriguez–Ubis et al., "Lanthanide Complexes of Polyacid Ligands Derived from 2,6–Bis (pyrazol–1–yl) pyridine, Pyrazine, and 6,6'–Bis(pyrazol–1–yl)–2,2'–bipyridine: Synthesis and Luminescence Properties," *Helvetica Chimica Acta* 80:86–96 (1997).
Hage, R., "Oxidation Catalysis by Biomimetic Manganese Complexes," *Recueil des Travaux Chimiques des Pays–Bas* 115 (9) :385–395 (1996).

* cited by examiner

*Primary Examiner*—John Kight
*Assistant Examiner*—Binta Robinson
(74) *Attorney, Agent, or Firm*—Hamilton, Brook, Smith & Reynolds, P.C.

(57) ABSTRACT

Compounds and methods of preparing compounds represented by structural formula (I):

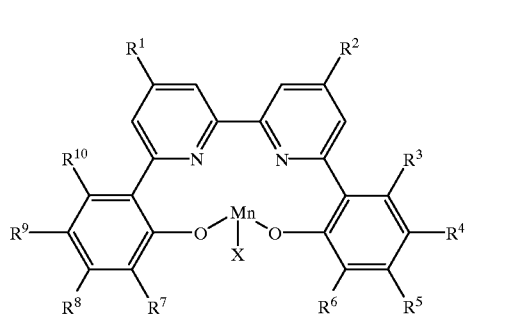

wherein X represents any suitable counter-anion;

$R^1$ and $R^2$ independently represent hydrogen, $C_{1-6}$ alkoxy or nitro;

$R^3$, $R^4$, $R^5$ and $R^6$ each independently represents hydrogen, hydroxy, halo, $C_{1-6}$ alkyl, $C_{2-6}$ alkenyl or $C_{1-6}$ alkoxy; and $R^7$, $R^8$, $R^9$ and $R^{10}$ each independently represents hydrogen, hydroxy, halo, $C_{1-6}$ alkyl, $C_{2-6}$ alkenyl or $C_{1-6}$ alkoxy.

Compounds represented by structural formula (I) are useful in treating or preventing free radical-associated diseases or conditions in mammals.

22 Claims, No Drawings

BIPYRIDINE MANGANESE COMPLEXES

RELATED APPLICATION

This application is a Continuation-in-Part of and claims priority under 35 U.S.C. § 119 to United Kingdom Patent Application No. GB 98 17 845.2, filed Aug. 17, 1998, the entire teachings of which are incorporated herein by reference.

BACKGROUND OF THE INVENTION

Molecular oxygen is an essential nutrient for nonfacultative aerobic organisms, including humans. Oxygen is used in many important ways, namely, as the terminal electronic acceptor in oxidative phosphorylation, in many dioxygenase reactions, including the synthesis of prostaglandins and of vitamin A from carotenoids, in a host of hydroxylase reactions, including the formation and modification of steroid hormones, and in both the activation and the inactivation of xenobiotics, including carcinogens. The extensive P-450 system uses molecular oxygen in a host of important cellular reactions. In a similar vein, nature employs free radicals in a large variety of enzymic reactions.

Excessive concentrations of various forms of oxygen and of free radicals can have serious adverse effects on living systems, including the peroxidation of membrane lipids, the hydroxylation of nucleic acid bases, and the oxidation of sulfhydryl groups and of other sensitive moieties in proteins. If uncontrolled, mutations and cellular death result.

Biological antioxidants include well-defined enzymes, such as superoxide dismutase, catalase, selenium glutathione peroxidase, and phospholipid hydroperoxide glutathione peroxidase. Nonenzymatic biological antioxidants include tocopherols and tocotrienols, carotenoids, quinones, bilirubin, ascorbic acid, uric acid, and metal-binding proteins. Various antioxidants, being both lipid and water soluble, are found in all parts of cells and tissues, although each specific antioxidant often shows a characteristic distribution pattern. The so-called ovothiols, which are mercaptohistidine derivatives, also decompose peroxides nonenzymatically.

Free radicals, particularly free radicals derived from molecular oxygen, are believed to play a fundamental role in a wide variety of biological phenomena. In fact, it has been suggested that much of what is considered critical illness may involve oxygen radical ("oxyradical") pathophysiology (Zimmermen J J (1991) *Chest* 100: 189S). Oxyradical injury has been implicated in the pathogenesis of pulmonary oxygen toxicity, adult respiratory distress syndrome (ARDS), bronchopulmonary dysplasia, sepsis syndrome, and a variety of ischemia-reperfuision syndromes, including myocardial infarction, stroke, cardiopulmonary bypass, organ transplantation, necrotizing enterocolitis, acute renal tubular necrosis, and other disease. Oxyradicals can react with proteins, nucleic acids, lipids, and other biological macromolecules producing damage to cells and tissues, particularly in the critically ill patient.

Free radicals are atoms, ions, or molecules that contain an unpaired electron (Pryor W A (1976) *Free Radicals in Biol.* 1: 1). Free radicals are usually unstable and exhibit short half-lives. Elemental oxygen is highly electronegative and readily accepts single electron transfers from cytochromes and other reduced cellular components; a portion of the $O_2$ consumed by cells engaged in aerobic respiration is univalently reduced to superoxide radical (•$O_2^-$) (Cadenas E (1989) *Ann. Rev. Biochem.* 58: 79). Sequential univalent reduction of •$O_2^-$ produces hydrogen peroxide ($H_2O_2$), hydroxyl radical (•OH), and water.

Free radicals can originate from many sources, including aerobic respiration, cytochrome P-450-catalysed monooxygenation reactions of drugs and xenobiotics (e.g., trichloromethyl radicals, $CCl_3$•, formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen creating two radicals H• and •OH. The hydroxyl radical, •OH, is the most reactive known in chemistry. It reacts with biomolecules and sets off chain reactions and can interact with the purine or pyrimidine bases of nucleic acids. Indeed, radiation-induced carcinogenesis may be initiated by free radical damage (Breimer L H (1988) *Brit. J. Cancer* 57: 6). Also for example, the "oxidative burst" of activated neutrophils produces abundant superoxide radical, which is believed to be an essential factor in producing the cytotoxic effect of activated neutrophils. Reperfusion of ischemic tissues also produces large concentrations of oxyradicals, typically superoxide (Gutteridge J M C and Halliwell B (1990) *Arch. Biochem. Biophys.* 283: 223). Moreover, superoxide may be produced physiologically by endothelial cells for reaction with nitric oxide, a physiological regulator, forming peroxynitrite, $ONOO^-$ which may decay and give rise to hydroxyl radical, •OH (Marletta M A (1989) *Trends Biochem. Sci.* 14: 488; Moncada et al. (1989) *Biochem. Pharmacol.* 38: 1709; Saran et al. (1990) *Free Rad. Res. Commun.* 10: 221; Beckman et al. (1990) *Proc. Natl. Acad. Sci. (U.S.A.)* 87: 1620). Additional sources of oxyradicals are "leakage" of electrons from disrupted mitochondrial or endoplasmic reticular electron transport chains, prostaglandin synthesis, oxidation of catecholamines, and platelet activation.

Oxygen, though essential for aerobic metabolism, can be converted to poisonous metabolites, such as the superoxide anion and hydrogen peroxide, collectively known as reactive oxygen species (ROS). Increased ROS formation under pathological conditions is believed to cause cellular damage through the action of these highly reactive molecules on proteins, lipids, and DNA. During inflammation, ROS are generated by activated phagocytic leukocytes; for example, during the neutrophil "respiratory burst", superoxide anion is generated by the membrane-bound NADPH oxidase. ROS are also believed to accumulate when tissues are subjected to ischemia followed by reperfusion.

Many free radical reactions are highly damaging to cellular components; they crosslink proteins, mutagenize DNA, and peroxidize lipids. Once formed, free radicals can interact to produce other free radicals and non-radical oxidants such as singlet oxygen ($^1O_2$) and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman E R (1992) *Science* 257: 1220).

•$O_2^-$ can also react, at a diffusion-limited rate, with NO; yielding peroxynitrite (Huie et al. (1993) *Free Rad. Res. Commun.* 18: 195).

It is also known that superoxide is involved in the breakdown of endothelium-derived vascular relaxing factor (EDRF), which has been identified as nitric oxide (NO), and that EDRF is protected from breakdown by superoxide dismutase. This suggests a central role for activated oxygen species derived from superoxide in the pathogenesis of vasospasm, thrombosis and atherosclerosis. See, for example Gryglewski R J et al., "Superoxide Anion is Involved in the Breakdown of Endothelium-derived Vascular Relaxing Factor", (1986) *Nature* 320: 454–456 and Palmer R M J et al., "Nitric Oxide Release Accounts for the Biological Activity of Endothelium Derived Relaxing Factor", (1987) *Nature* 327: 523–526.

Aerobic cells generally contain a number of defences against the deleterious effects of oxyradicals and their reaction products. Superoxide dismutases (SODs) catalyse the reaction:

$$2 \cdot O_2^- + 2H^+ \rightarrow O_2 + H_2O_2$$

which removes superoxide and forms hydrogen peroxide. $H_2O_2$ is not a radical, but it is toxic to cells; it is removed by the enzymatic activities of catalase and glutathione peroxidase (GSH-Px). Catalase catalyses the reaction:

$$2H_2O_2 \rightarrow 2H_2O + O_2$$

and removes hydrogen peroxide and forms water and oxygen. GSH-Px removes hydrogen peroxide by using it to oxidise reduced glutathione (GSH) into oxidised glutathione (GSSG) according to the following reaction:

$$2GSH + H_2O_2 \rightarrow GSSG + 2H_2O$$

Other enzymes, such as phospholipid hydroperoxide glutathione peroxidase (PLOOH-GSH-Px), convert reactive phopholipid hydroperoxides, free fatty acid hydroperoxides, and cholesterol hydroperoxides to corresponding harmless fatty acid alcohols. Glutathione S-transferases also participate in detoxifying organic peroxides. In the absence of these enzymes and in presence of transition metals, such as iron or copper, superoxide and hydrogen peroxide can participate in the following reactions which generate the extremely reactive hydroxyl radical •OH⁻:

$$\cdot O_2^- + Fe^{3+} \rightarrow O_2 + Fe^{2+}$$

$$H_2O_2 + Fe^{2+} \rightarrow \cdot OH + OH^- + Fe^{3+}$$

In addition to enzymatic detoxification of free radicals and oxidant species, a variety of low molecular weight antioxidants such as glutathione, ascorbate, tocopherol, ubiquinone, bilirubin, and uric acid serve as naturally-occurring physiological antioxidants (Krinsky N I (1992) *Proc. Soc. Exp. Biol. Med.* 200: 248–54). Carotenoids are another class of small molecule antioxidants and have been implicated as protective agents against oxidative stress and chronic diseases. Canfield et al. (1992) *Proc. Soc. Exp. Biol. Med.* 200: 260 summarize reported relationships between carotenoids and various chronic diseases, including coronary heart disease, cataract, and cancer. Carotenoids dramatically reduce the incidence of certain premalignant conditions, such as leukoplakia, in some patients.

In an effort to prevent the damaging effects of oxyradical formation during reoxygenation of ischemic tissues, a variety of antioxidants have been used. One strategy for preventing oxyradical-induced damage is to inhibit the formation of oxyradicals such as superoxide. Iron ion chelators, such as desferrioxamine (also called deferoxamine or Desferal) and others, inhibit iron ion-dependent •OH generation and thus act as inhibitors of free radical formation (Gutteridge et al. (1979) *Biochem. J.* 184: 469; Halliwell B (1989) *Free Radical Biol. Med.* 7: 645; Van der Kraaij et al. (1989) *Circulation* 80: 158). Amino-steroid-based antioxidants such as the 21-aminosteroids terms "lazaroids" (e.g, U74006F) have also been proposed as inhibitors of oxyradical formation. Desferrioxamine, allopurinol, and other pyrazolopyrimidines such as oxypurinol, have also been tested for preventing oxyradical formation in a myocardial stunning model system (Bolli et al. (1989) *Circ. Res.* 65: 607) and following hemorrhagic and endotoxic shock (DeGarvilla et al. (1992) *Drug Devel. Res.* 25: 139). However, each of these compounds has notable drawbacks for therapeutic usage. For example, deferoxamine is not an ideal iron chelator and its cellular penetration is quite limited.

Another strategy for preventing oxyradical-induced damage is to catalytically remove oxyradicals such as superoxide once they have been formed. Superoxide dismutase and catalase have been extensively explored, with some success, as protective agents when added to reperfusates in many types of experiments or when added pre-ischemia (reviewed in Gutteridge J M C and Halliwell B (1990) op.cit.). The availability of recombinant superoxide dismutase has allowed more extensive evaluation of the effect of administering SOD in the treatment or prevention of various medical conditions including reperfusion injury of the brain and spinal cord (Uyama et al. (1990) *Free Radic. Biol. Med.* 8: 265; Lim et al. (1986) *Ann. Thorac. Surg.* 42: 282), endotoxemia (Schneider et al. (1990) *Circ. Shock* 30: 97; Schneider et al. (1989) *Prog. Clin. Biol. Res.* 308: 913, and myocardial infarction (Patel et al. (1990) *Am. J. Physiol.* 258: H369; Mehta et al. (1989) *Am. J. Physiol.* 257: H1240; Nejima et al. (1989) *Circulation* 79: 143; Fincke et al. (1988) *Arzneimittelforschung* 38: 138; Ambrosio et al. (1987) *Circulation* 75: 282), and for osteoarthritis and intestinal ischemia (Vohra et al. (1989) *J. Pediatr. Surg.* 24: 893; Flohe L. (1988) *Mol. Cell. Biochem.* 84: 123). Superoxide dismutase also has been reported to have positive effects in treating systemic lupus erythematosus, Crohn's disease, gastric ulcers, oxygen toxicity, burned patients, renal failure attendant to transplantation, and herpes simplex infection.

An alternative strategy for preventing oxyradical-induced damage is to scavenge oxyradicals such as superoxide once these have been formed, typically by employing small molecule scavengers which act stoichiometrically rather than catalytically. Congeners of glutathione have been used in various animal models to attenuate oxyradical injury. For example, N-2-mercaptopropionylglycine has been found to confer protective effects in a canine model of myocardial ischemia and reperfusion (Mitsos et al. (1986) *Circulation* 73: 1077) and N-acetylcysteine ("Mucomyst") has been used to treat endotoxin toxicity in sheep (Bernard et al. (1984) *J. Clin. Invest.* 73: 1772). Dimethyl thiourea (DMTU) and butyl-α-phenylnitrone (BPN) are believed to scavenge the hydroxyl radical, •OH, and have been shown to reduce ischemia-reperfusion injury in rat myocardium and in rabbits (Vander Heide et al. (1987) *J. Appl. Physiol.* 63: 2426). Mannitol has also been used as a free radical scavenger to reduce organ injury during reoxygenation (Fox RB (1984) *J. Clin. Invest.* 74: 1456; Ouriel et al. (1985) *Circulation* 72: 254).

Thus, application of inhibitors of oxyradical formation and/or enzymes that remove superoxide and hydrogen peroxide and/or small molecule oxyradical scavengers have all shown promise for preventing re-oxygenation damage present in a variety of ischemic pathological states and for treating or preventing various disease states associated with free radicals. However, each of these categories contains several drawbacks. For example, inhibitors of oxyradical formation typically chelate transition metals which are used in essential enzymatic processes in normal physiology and respiration; moreover, even at very high doses, these inhibitors do not completely prevent oxyradical formation. Superoxide dismutases and catalase are large polypeptides which are expensive to manufacture, do not penetrate cells or the blood-brain barrier, and generally require parenteral routes of administration. Free radical scavengers act stoichiometrically and are thus easily depleted and must be administered in high dosages to be effective.

The complex formed between the chelator desferrioxamine and manganese has SOD activity and has shown some activity in biological models but the instability of the metal ligand complex apparently precludes its pharmaceutical use. Porphyrin-manganese complexes have been shown to protect bacteria from paraquat toxicity and to promote the aerobic survival of SOD-deficient *E. coli* mutants. A class of manganese macrocyclic ligand complexes with SOD activity has also been described with one prototype reportedly showing protection in a model for myocardial ischemia-reperfusion injury (Black et al. (1994) *J. Pharmacol. Exp. Ther.* 270: 1208).

WO94/13300 (and U.S. Pat. No. 5,403,834 and the related applications U.S. Ser. No. 08/380,731 and U.S. Ser. No. 08/479,697), U.S. Pat. No. 5,696,109, WO96/40148 and WO96/40149 each disclose salen-transition metal complexes, including salen-manganese complexes, such as salen-Mn (III) complexes of general formula

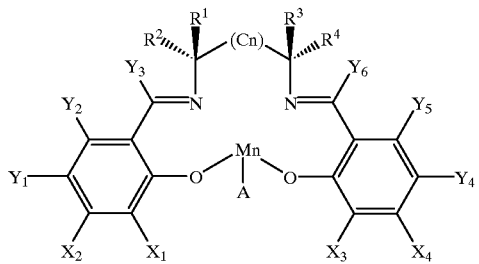

wherein $R^1$ to $R^4$, $Y_1$ to $Y_6$, $X_1$ to $X_4$, A and n are as separately defined in each of the specifications referred to above, as having antioxidant and/or free radical scavenging properties; the compounds are indicated to have superoxide dismutase activity and/or catalase activity.

WO95/10185 and WO96/09053 disclose manganese porphyrin derivatives of general formula

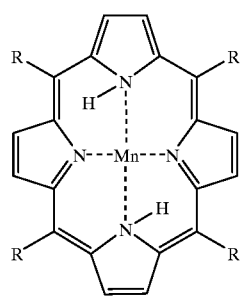

wherein R is as defined therein, as mimetics of superoxide dismutase.

WO96/39396 discloses manganese or iron complexes of nitrogen-containing fifteen-membered macrocyclic ligands of general formula

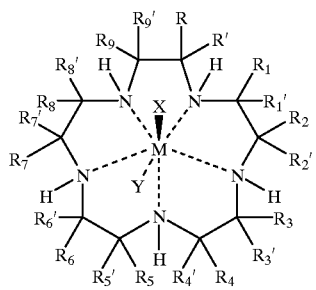

wherein $R_1$ to $R_9$, $R_1'$ to $R_9'$, X, Y and M are as defined therein, as superoxide dismutase mimics.

It is therefore an object of the present invention to provide further compounds, in particular manganese complexes, which are SOD, CAT or POD mimetics and which are therefore of utility as prophylactic and therapeutic agents.

SUMMARY OF THE INVENTION

The present invention relates to compounds which are effective as superoxide dismutase (SOD), and/or catalase (CAT), and/or peroxidase (POD) mimetics and which, accordingly, have antioxidant and/or free radical scavenging properties and function as in vivo antioxidants. In particular the present invention relates to manganese complexes of bipyridine derivatives, pharmaceutical formulations containing them, processes for their preparation and intermediates in such processes, and the use of such compounds in prophylaxis and therapy.

The manganese bipyridine complexes can be represented by structural formula (I):

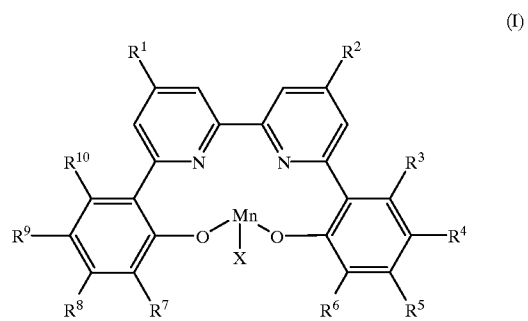

(I)

In structural formula (I), X represents any suitable counteranion; $R^1$ and $R^2$, independently, represent hydrogen, $C_{1-6}$ alkoxy or nitro; $R^3$, $R^4$, $R^5$ and $R^6$ each, independently, represents hydrogen, hydroxy, halo, $C_{1-6}$ alkyl, $C_{2-6}$ alkenyl or $C_{1-6}$ alkoxy; and $R^7$, $R^8$, $R^9$ and $R^{10}$ each, independently, represents hydrogen, hydroxy, halo, $C_{1-6}$ alkyl, $C_{2-6}$ alkenyl or $C_{1-6}$ alkoxy. Solvates of the compounds of formula (I) are also included within the scope of the present invention.

The foregoing and other objects, features and advantages of the invention will be apparent from the following more particular description of preferred embodiments of the invention.

DETAILED DESCRIPTION OF THE INVENTION

Certain compounds of formula (I) can exist in stereoisomeric forms (e.g. they can contain one or more asymmetric carbon atoms or can exhibit cis-trans isomerism). The individual stereoisomers (enantiomers and diastereoisomers) and mixtures of these are included within the scope of the present invention. Likewise, it is understood that certain compounds of formula (I) can exist in tautomeric forms and these are also included within the scope of the present invention.

Suitable values for the various groups listed above within the definitions for $R^1$ to $R^{10}$ are as follows:

Halo is, for example, fluoro, chloro, bromo or iodo; preferably it is fluoro, chloro or bromo, more preferably fluoro;

$C_{1-6}$ alkyl is, for example, methyl, ethyl, n-propyl, isopropyl, n-butyl, isobutyl, sec-butyl, tert-butyl, n-pentyl, isopentyl, sec-pentyl, n-hexyl, isohexyl and sec-hexyl; preferably it is methyl, ethyl, isopropyl, tert-butyl and n-hexyl, more preferably methyl;

$C_{2-6}$ alkenyl is, for example, ethenyl, propenyl, allyl, but-1-enyl, but-2-enyl, 2-methyl-prop-1-enyl; preferably it is ethenyl or allyl, more preferably allyl;

$C_{1-6}$ alkoxy is, for example, methoxy, ethoxy, n-propoxy, isopropoxy, n-butoxy, isobutoxy, sec-butoxy, tert-butoxy, n-pentoxy, isopentoxy, sec-pentoxy, n-hexyloxy, iso-hexyloxy and sec-hexyloxy; preferably it is methoxy or ethoxy, more preferably methoxy.

The counter anion X can represent any suitable anion with which the complex of formula (I) can be formed. Suitable examples include halide, formate, acetate, propionate, butyrate, valerate, methoxide, ethoxide, $PF_6$ or triflate. X is typically chloride, bromide, fluoride, methoxide or acetate. Preferably X represents acetate or chloride.

Mn is in the 3+ oxidation state in the compound of formula (I); also encompassed by the present invention are the compounds of formula (Ia)

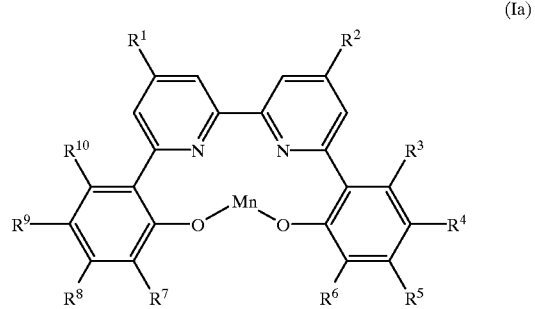

(Ia)

wherein $R^1$ to $R^{10}$ are as defined above, in which Mn is in the 2+ oxidation state.

Thus the phenyl ring carrying the groups $R^3$ to $R^6$ may be unsubstituted (where each of $R^3$ to $R^6$ represents hydrogen) or may be mono-, di-, tri- or tetra-substituted at any of the available positions of the ring with the other groups defined above for $R^3$ to $R^6$; where the phenyl ring is di-, tri- or tetra-substituted each of the substituents may be the same or may be different. Similar considerations apply in respect of the phenyl ring carrying the groups $R^7$ to $R^{10}$.

In an embodiment $R^1$ and $R^2$ independently represent hydrogen, methoxy or ethoxy; preferably $R^1$ and $R^2$ represent hydrogen.

In another embodiment $R^1$ and $R^2$ are identical.

In an embodiment at least one of $R^3$, $R^4$, $R^5$ and $R^6$ represents hydrogen.

In a further embodiment at least one of $R^7$, $R^8$, $R^9$ and $R^{10}$ represents hydrogen.

In a preferred embodiment at least one of $R^3$, $R^4$, $R^5$ and $R^6$ represents hydrogen and at least one of $R^7$, $R^8$, $R^9$ and $R^{10}$ represents hydrogen.

In a more preferred embodiment each of the phenyl rings are independently either unsubstituted or are mono- or di-substituted.

In an embodiment the phenyl ring carrying the groups $R^3$ to $R^6$ is substituted identically to the phenyl ring carrying the groups $R^7$ to $R^{10}$; identically in this context applies not only to the nature of the substituents but also to their positions.

In another embodiment the phenyl ring carrying the groups $R^3$ to $R^6$ is substituted non-identically to the phenyl ring carrying the groups $R^7$ to $R^{10}$; non-identically in this context has the opposite meaning to identically as defined above.

In another embodiment each of $R^3$ to $R^6$ represents hydrogen, hydroxy, fluoro, methyl, ethyl, isopropyl, tert-butyl, n-hexyl, propenyl (especially allyl), methoxy or ethoxy.

In a preferred embodiment $R^3$ represents hydrogen or methoxy, more preferably hydrogen.

In a preferred embodiment $R^4$ represents hydrogen, fluoro, methyl, ethyl, isopropyl, tert-butyl, propenyl (especially allyl) or methoxy.

In a preferred embodiment $R^5$ represents hydrogen, methyl or ethyl, more preferably hydrogen or methyl, especially hydrogen.

In a preferred embodiment $R^6$ represents hydrogen, hydroxy, fluoro, methyl, n-hexyl, propenyl (especially allyl), methoxy or ethoxy.

In another embodiment each of $R^7$ to $R^{10}$ represents hydrogen, hydroxy, fluoro, methyl, ethyl, isopropyl, n-hexyl, propenyl (especially allyl), methoxy or ethoxy.

In a preferred embodiment $R^7$ represents hydrogen, hydroxy, fluoro, methyl, n-hexyl, propenyl (especially allyl), methoxy or ethoxy.

In a preferred embodiment $R^1$ represents hydrogen, methyl or ethyl, more preferably hydrogen or methyl.

In a preferred embodiment $R^9$ represents hydrogen, fluoro, methyl, ethyl, isopropyl, tert-butyl, propenyl (especially allyl) or methoxy.

In a preferred embodiment $R^{10}$ represents hydrogen or methoxy, more preferably hydrogen.

In a further embodiment three of $R^3$ to $R^6$ represent hydrogen and the remaining one, preferably $R^4$ or $R^6$, is selected from the groups as defined above, preferably hydroxy, fluoro, methyl, ethyl, isopropyl, n-hexyl, propenyl (especially allyl), methoxy or ethoxy.

In a further embodiment two of $R^3$ to $R^6$ represent hydrogen and the remaining two, preferably $R^4$ and $R^6$ or $R^5$ and $R^6$, are independently selected from the groups as defined above, preferably methyl, methoxy or propenyl (especially allyl).

In a further embodiment three of $R^7$ to $R^{10}$ represent hydrogen and the remaining one, preferably $R^7$, $R^8$ or $R^9$, is selected from the groups as defined above, preferably hydroxy, fluoro, methyl, ethyl, isopropyl, n-hexyl, propenyl (especially allyl), methoxy or ethoxy.

In a further embodiment two of $R^7$ to $R^{10}$ represent hydrogen and the remaining two, preferably $R^7$ and $R^9$, are independently selected from the groups as defined above, preferably methyl or methoxy.

In a preferred embodiment there is provided a compound of formula (I) as defined above wherein $R^1$, $R^2$, $R^3$, $R^8$ and $R^{10}$ each represent hydrogen; $R^4$ and $R^9$ are independently selected from hydrogen and methoxy; $R^5$ is selected from hydrogen and methyl; $R^6$ and $R^7$ are independently selected from hydrogen, methyl and methoxy; and X represents acetate or chloride, more especially acetate; or a solvate thereof.

It is to be understood that the present invention covers all combinations of particular and preferred groups as described above.

In a particularly preferred embodiment there is provided a compound of formula (I) as defined above selected from the group comprising:

6,6'-Bis(2-hydroxyphenyl)-2,2'-bipyridine-manganese (III) acetate;
6,6'-Bis(2-hydroxy-5-methoxyphenyl)-2,2'-bipyridine-manganese (III) acetate;
6,6'-Bis(2-hydroxy-3-methoxyphenyl)-2,2'-bipyridine-manganese (III) acetate;
6,6'-Bis(2-hydroxy-3-ethoxyphenyl)-2,2'-bipyridine-manganese (III) acetate;
6,6'-Bis(2-hydroxy-3-methoxy-5-methylphenyl)-2,2'-bipyridine-manganese (III) acetate;
6,6'-Bis(2-hydroxy-5-fluorophenyl)-2,2'-bipyridine-manganese (III) acetate;
6,6'-Bis(2-hydroxy-5-methylphenyl)-2,2'-bipyridine-manganese (III) acetate;
6,6'-Bis(2-hydroxy-3-methylphenyl)-2,2'-bipyridine-manganese (III) acetate;
6,6'-Bis(2-hydroxy-3,5-dimethylphenyl)-2,2'-bipyridine-manganese (III) acetate;
6,6'-Bis(2-hydroxy-3-fluorophenyl)-2,2'-bipyridine-manganese (III) acetate;
6,6'-Bis(2-hydroxy-4-methylphenyl)-2,2'-bipyridine-manganese (III) acetate;
6,6'-Bis(2,3-dihydroxyphenyl)-2,2'-bipyridine-manganese (II) acetate;
6,6'-Bis(2-hydroxy-6-methoxyphenyl)-2,2'-bipyridine-manganese (III) acetate;
6,6'-Bis(2-hydroxy-5-t-butylphenyl)-2,2'-bipyridine-manganese (III) acetate;
6,6'-Bis(5-allyl-2-hydroxy-3-methoxyphenyl)-2,2'-bipyridine-manganese (III) acetate;
6-(2-Hydroxy-5-methoxyphenyl)-6'-(2-hydroxy-3-methylphenyl)-2,2'-bipyridine-manganese (III) acetate;
6,6'-Bis(3-allyl-2-hydroxyphenyl)-2,2'-bipyridine-manganese (III) acetate;
6,6'-Bis(3-hexyl-2-hydroxy phenyl)-2,2'-bipyridine-manganese (III) acetate;
6-(2-Hydroxyphenyl)-2-hydroxy-4-methylphenyl)-2,2'-bipyridine-manganese (III) acetate;
6-(2-Hydroxy-3-methoxyphenyl)-6'-(2-hydroxy-4-methylphenyl)-2,2'-bipyridine-manganese (III) acetate;
6-(2-Hydroxy-5-methoxyphenyl)-6'-(2-hydroxy-4-methylphenyl)-2,2'-bipyridine-manganese (III) acetate;
6-(2-Hydroxy-3-methylphenyl)-6'-(2-hydroxy-4-methylphenyl)-2,2'-bipyridine-manganese (III) acetate;
6-(3-Fluoro-2-hydroxyphenyl)-6'-(2-hydroxy-4-methylphenyl)-2,2'-bipyridine-manganese (III) acetate;
6-(3,4-Dimethyl-2-hydroxyphenyl)-6'-(2-hydroxy-4-methylphenyl)-2,2 '-bipyridine-manganese (III) acetate;
6-(2-Hydroxy-4-methylphenyl)-6'-(2-hydroxy-5-methylphenyl)-2,2'-bipyridine-manganese (III) acetate;
6-(2-Hydroxyphenyl)-6'-(2-hydroxy-3-methoxyphenyl)-2,2'-bipyridine-manganese (III) acetate;
6-(2-Hydroxy-3-methoxyphenyl)-6'-(2-hydroxy-5-methoxyphenyl)-2,2'-bipyridine-manganese (III) acetate;
6-(2-Hydroxy-3-methoxyphenyl)-6'-(2-hydroxy-3-methylphenyl)-2,2'-bipyridine-manganese (III) acetate;
6-(2-Hydroxy-3-hexylphenyl)-6'-(2-hydroxy-3-methoxyphenyl)-2,2'-bipyridine-manganese (III) acetate;
6-(3,4-Dimethyl-2-hydroxyphenyl)-6'-(2-hydroxy-3-methoxyphenyl)-2,2'-bipyridine-manganese (III) acetate;
6-(2-Hydroxy-3-methoxyphenyl)-6'-(2-hydroxy-5-methylphenyl)-2,2'-bipyridine-manganese (III) acetate;
6-(2-Hydroxyphenyl)-6'-(2-hydroxy-5-methoxyphenyl)-2,2'-bipyridine-manganese (III) acetate;
6-(3-Hexyl-2-hydroxyphenyl)-6'-(2-hydroxy-5-methoxyphenyl)-2,2'-bipyridine-manganese (III) acetate;
6-(5-Fluoro-2-hydroxyphenyl)-6'-(2-hydroxy-5-methoxyphenyl)-2,2'-bipyridine-manganese (III) acetate;
6-(3,4-Dimethyl-2-hydroxyphenyl)-6'-(2-hydroxy-5-methoxyphenyl)-2,2'-bipyridine-manganese (III) acetate;
6-(2-Hydroxy-5-methoxyphenyl)-6'-(2-hydroxy-5-methylphenyl)-2,2'-bipyridine-manganese (III) acetate;
6-(2-Hydroxy-5-methoxyphenyl)-6'-(2-hydroxy-3-methoxy-5-methylphenyl)-2,2'-bipyridine-manganese (III) acetate;
6-(2-Hydroxy-5-methoxyphenyl)-6'-(5-allyl-2-hydroxy-3-methoxyphenyl)-2,2'-bipyridine-manganese (III) acetate;
6-(2-Hydroxy-3-methoxyphenyl)-6'-(5-allyl-2-hydroxy-3-methoxyphenyl)-2,2'-bipyridine-manganese (III) acetate;
6,6'-Bis(5-ethyl-2-hydroxyphenyl)-2,2'-bipyridine-manganese (III) acetate;
6,6'-Bis(2-hydroxy-5-isopropylphenyl)-2,2'-bipyridine-manganese (III) acetate;
6,6'-Bis(4-ethyl-2-hydroxyphenyl)-2,2'-bipyridine-manganese (III) acetate;
6,6'-Bis(2-hydroxy-3-methoxyphenyl)-2,2'-bipyridine-manganese (III) chloride; and solvates thereof, particularly pharmaceutically acceptable solvates thereof.

In a further particularly preferred embodiment there is provided a compound of formula (I) as defined above selected from the group comprising:

6,6'-Bis(2-hydroxyphenyl)-2,2'-bipyridine-manganese (III) chloride;
6,6'-Bis(2-hydroxy-5-methoxyphenyl)-2,2'-bipyridine-manganese (III) chloride;
6,6'-Bis(2-hydroxy-3-ethoxyphenyl)-2,2'-bipyridine-manganese (III) chloride;
6,6'-Bis(2-hydroxy-3-methoxy-5-methylphenyl)-2,2'-bipyridine-manganese (III) chloride;
6,6'-Bis(2-hydroxy-5-fluorophenyl)-2,2'-bipyridine-manganese (III) chloride;
6,6'-Bis(2-hydroxy-5-methylphenyl)-2,2'-bipyridine-manganese (III) chloride;
6,6'-Bis(2-hydroxy-3-methylphenyl)-2,2'-bipyridine-manganese (III) chloride;
6,6'-Bis(2-hydroxy-3,5-dimethylphenyl)-2,2'-bipyridine-manganese (III) chloride;
6,6'-Bis(2-hydroxy-3-fluorophenyl)-2,2'-bipyridine-manganese (III) chloride;
6,6'-Bis(2-hydroxy-4-methylphenyl)-2,2'-bipyridine-manganese (III) chloride;

6,6'-Bis(2,3-dihydroxy phenyl)-2,2'-bipyridine-manganese (III) chloride;

6,6'-Bis(2-hydroxy-6-methoxyphenyl)-2,2'-bipyridine-manganese (III) chloride;

6,6'-Bis(2-hydroxy-5-t-butylphenyl)-2,2'-bipyridine-manganese (III) chloride;

6,6'-Bis(5-allyl-2-hydroxy-3-methoxyphenyl)-2,2'-bipyridine-manganese (III) chloride;

6-(2-Hydroxy-5-methoxyphenyl)-6'-(2-hydroxy-3-methylphenyl)-2,2'-bipyridine-manganese (III) chloride;

6,6'-Bis(3-allyl-2-hydroxyphenyl)-2,2'-bipyridine-manganese (III) chloride;

6,6'-Bis(3-hexyl-2-hydroxyphenyl)-2,2'-bipyridine-manganese (III) chloride;

6-(2-Hydroxyphenyl)-6'-(2-hydroxy-4-methylphenyl)-2,2'-bipyridine-manganese (III) chloride;

6-(2-Hydroxy-3-methoxyphenyl)-6'-(2-hydroxy-4-methylphenyl)-2,2'-bipyridine-manganese (III) chloride;

6-(2-Hydroxy-5-methoxyphenyl)-6'-(2-hydroxy-4-methylphenyl)-2,2'-bipyridine-manganese (III) chloride;

6-(2-Hydroxy-3-methylphenyl)-6'-(2-hydroxy-4-methylphenyl)-2,2'-bipyridine-manganese (III) chloride;

6-(3-Fluoro-2-hydroxyphenyl)-6'-(2-hydroxy-4-methylphenyl)-2,2'-bipyridine-manganese (III) chloride;

6-(3,4-Dimethyl-2-hydroxyphenyl)-6'-(2-hydroxy-4-methylphenyl)-2,2'-bipyridine-manganese (III) chloride;

6-(2-Hydroxy-4-methylphenyl)-6'-(2-hydroxy-5-methylphenyl)-2,2'-bipyridine-manganese (III) chloride;

6-(2-Hydroxyphenyl)-6'-(2-hydroxy-3-methoxyphenyl)-2,2'-bipyridine-manganese (III) chloride;

6-(2-Hydroxy-3-methoxyphenyl)-6'-(2-hydroxy-5-methoxyphenyl)-2,2'-bipyridine-manganese (III) chloride;

6-(2-Hydroxy-3-methoxyphenyl)-6'-(2-hydroxy-3-methylphenyl)-2,2'-bipyridine-manganese (III) chloride;

6-(2-Hydroxy-3-hexylphenyl)-6'-(2-hydroxy-3-methoxyphenyl)-2,2'-bipyridine manganese (III) chloride;

6-(3,4-Dimethyl-2-hydroxyphenyl)-6'-(2-hydroxy-3-methoxyphenyl)-2,2'-bipyridine-manganese (III) chloride;

6-(2-Hydroxy-3-methoxyphenyl)-6'-(2-hydroxy-5-methylphenyl)-2,2'-bipyridine-manganese (III) chloride;

6-(2-Hydroxyphenyl)-6'-(2-hydroxy-5-methoxyphenyl)-2,2'-bipyridine-manganese (III) chloride;

6-(3-Hexyl-2-hydroxyphenyl)-6'-(2-hydroxy-5-methoxyphenyl)-2,2'-bipyridine-manganese (III) chloride;

6-(5-Fluoro-2-hydroxyphenyl)-6'-(2-hydroxy-5-methoxyphenyl)-2,2'-bipyridine-manganese (III) chloride;

6-(3,4-Dimethyl-2-hydroxyphenyl)-6'-(2-hydroxy-5-methoxyphenyl)-2,2'-bipyridine-manganese (III) chloride;

6-(2-Hydroxy-5-methoxyphenyl)-6'-(2-hydroxy-5-methylphenyl)-2,2'-bipyridine-manganese (III) chloride;

6-(2-Hydroxy-5-methoxyphenyl)-6'-(2-hydroxy-3-methoxy-5-methylphenyl)-2,2'-bipyridine-manganese (III) chloride;

6-(2-Hydroxy-5-methoxyphenyl)-6'-(5-allyl-2-hydroxy-3-methoxyphenyl)-2,2'-bipyridine-manganese (III) chloride;

6-(2-Hydroxy-3-methoxyphenyl)-6'-(5-allyl-2-hydroxy-3-methoxyphenyl)-2,2'-bipyridine-manganese (III) chloride;

6,6'-Bis(5-ethyl-2-hydroxyphenyl)-2,2'-bipyridine-manganese (III) chloride;

6,6'-Bis(2-hydroxy-5-isopropylphenyl)-2,2'-bipyridine-manganese (III) chloride;

6,6'-Bis(4-ethyl-2-hydroxyphenyl)-2,2'-bipyridine-manganese (III) chloride; and solvates thereof, particularly pharmaceutically acceptable solvates thereof.

In an especially preferred embodiment there is provided a compound of formula (I) as defined above selected from the group comprising:

6,6'-Bis(2-hydroxyphenyl)-2,2'-bipyridine-manganese (III) acetate;

6,6'-Bis(2-hydroxy-5-methoxyphenyl)-2,2'-bipyridine-manganese (III) acetate;

6,6'-Bis(2-hydroxy-3-methoxyphenyl)-2,2'-bipyridine-manganese (III) acetate;

6,6'-Bis(2-hydroxy-3-methylphenyl)-2,2'-bipyridine-manganese (III) acetate;

6-(3,4-Dimethyl-2-hydroxyphenyl)-6'-(2-hydroxy-5-methoxyphenyl)-2,2'-bipyridine-manganese (III) acetate;

6-(2-Hydroxy-5-methoxyphenyl)-6'-(2-hydroxy-5-methylphenyl)-2,2'-bipyridine-manganese (III) acetate; and solvates thereof, particularly pharmaceutically acceptable solvates thereof.

In a further especially preferred embodiment there is provided a compound of formula (I) as defined above selected from the group comprising: solvates thereof, particularly pharmaceutically acceptable solvates thereof.

6,6'-Bis(2-hydroxyphenyl)-2,2'-bipyridine-manganese (III) chloride;

6,6'-Bis(2-hydroxy-5-methoxyphenyl)-2,2'-bipyridine-manganese (III) chloride;

6,6'-Bis(2-hydroxy-3-methoxyphenyl)-2,2'-bipyridine-manganese (III) chloride;

6,6'-Bis(2-hydroxy-3-methylphenyl)-2,2'-bipyridine-manganese (III) chloride;

6-(3,4-Dimethyl-2-hydroxyphenyl)-6'-(2-hydroxy-5-methoxyphenyl)-2,2'-bipyridine-manganese (III) chloride;

6-(2-Hydroxy-5-methoxyphenyl)-6'-(2-hydroxy-5-methylphenyl)-2,2'-bipyridine-manganese (III) chloride; and solvates thereof, particularly pharmaceutically acceptable solvates thereof.

According to a further aspect of the present invention there is provided a process for the preparation of a compound of formula (I) as defined above which comprises the reaction of a compound of formula (II)

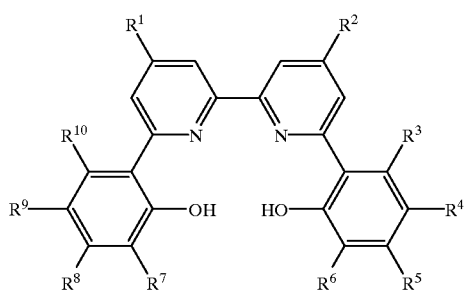

(II)

wherein $R^1$ to $R^{10}$ are as defined above, with an appropriate manganese reagent containing the anion X.

Thus, for example to prepare the compounds of formula (I) in which X represents acetate the reaction would be between the ligand of formula (II) and manganese (II) acetate tetrahydrate. Suitable manganese reagents can be used to prepare certain compounds of formula (I) in which X is otherwise defined; however, reaction with certain manganese reagents do not result in complexation as is the case, for example, with manganese (II) chloride. The reaction is typically carried out in an appropriate solvent, such as methanol, ethanol, DMF, isopropyl alcohol or butanol at temperatures up to the reflux temperature of the solvent, but preferably at temperatures between 0 and 25° C.

Alternatively, compounds of formula (I) in which X represents acetate can be converted using appropriate reagents to compounds of formula (I) in which X is otherwise defined. For example, exchange of X from acetate to chloride can be achieved by reaction with sodium chloride, suitably using a 5%–15% aqueous solution, the reaction typically being carried out in an aqueous, methanolic or ethanolic solution at temperatures up to the reflux temperature of the solvent, but preferably at temperatures between 0 and 25° C.

The compounds of formulae (II), wherein $R^3$ to $R^6$ are identical respectively to $R^{10}$ to $R^7$ (i.e. the two phenyl rings are substituted identically), may be prepared by reaction of the corresponding bipyridine derivative of formula (III)

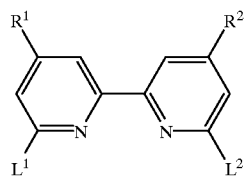

(III)

wherein $R^1$ and $R^2$ are as defined above and $L^1$ and $L^2$ are each, independently, a suitable leaving group, with the boronic acid derivative of formula (IV)

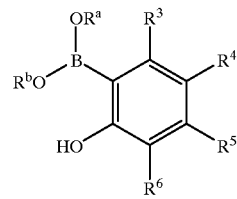

(IV)

wherein $R^3$ to $R^6$ are as defined above; and $R^a$ and $R^b$ represent hydrogen or $C_{1-6}$ alkyl; or $R^a$ and $R^b$ are linked to form a straight-chain or branched $C_{2-6}$ alkylene group.

Typically the reaction is carried out in an appropriate solvent such as propanol, 1,2-dimethoxyethane, ethanol or toluene at a temperature up to, but preferably at, the reflux temperature of the solvent; the reaction can typically take from between 2 to 24 hours. The reaction is typically performed in the presence of a base, such as sodium carbonate or triethylamine, and in the presence of a suitable palladium reagent, such as tetrakis(triphenylphosphine)palladium, bis(triphenylphosphine)palladium (II) chloride or [1,4-bis(diphenylphosphino)butane] palladium (II) chloride.

$L^1$ and $L^2$ are each, independently, preferably halo, more preferably chloro, bromo or iodo, most preferably bromo.

Alternatively, the compounds of formula (II) may be prepared by reaction of the bipyridine derivative of formula (V)

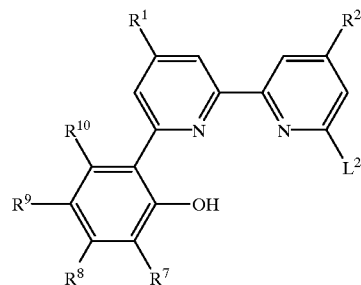

(V)

wherein $R^1$, $R^2$, $R^7$ to $R^{10}$ and $L^2$ are as defined above, with the boronic acid derivative of formula (IV) as defined above.

Alternatively, the compounds of formula (II) may be prepared by reaction of the bipyridine derivative of formula (VI)

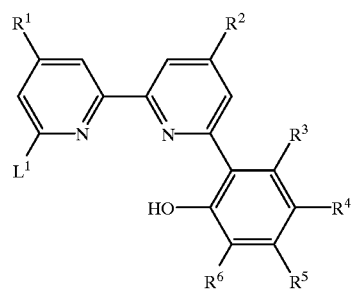

(VI)

wherein $R^1$, $R^2$, $R^3$ to $R^6$ and $L^1$ are as defined above, with the boronic acid derivative of formula (VII)

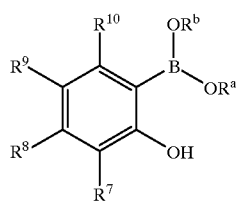

(VII)

wherein $R^7$ to $R^{10}$, $R^a$ and $R^b$ are as defined above.

These reactions to prepare the compounds of formulae (II) are typically carried out under similar conditions to the reaction between the compounds of formulae (III) and (IV) as described above.

The compound of formula (V) as defined above may be prepared by a similar reaction of a compound of formula (III) as defined above with a compound of formula (VII) as defined above. The compound of formula (VI) as defined above may be prepared by a similar reaction of a compound of formula (III) as defined above with a compound of formula (IV) as defined above. In these reactions, however, the compound of formula (III) is in excess to ensure that predominantly displacement of only one of leaving groups $L^1$ or $L^2$ occurs.

Where $R^1$ and $R^2$ are different, reaction of the compound of formula (III) with a compound of formula (IV) or (VI) will in fact result in the preparation of two isomeric products wherein respectively each leaving group $L^1$ and $L^2$ reacts, even though an excess of the compound of formula (III) means the displacement of both leaving groups is minimized; the relative yields of the two isomers will be dependent on the respective natures of $R^1$ and $R^2$ since this will influence the relative displacability of the leaving groups $L^1$ and $L^2$ on each pyridine ring. Reaction Scheme 1 below is a representative illustration of this aspect.

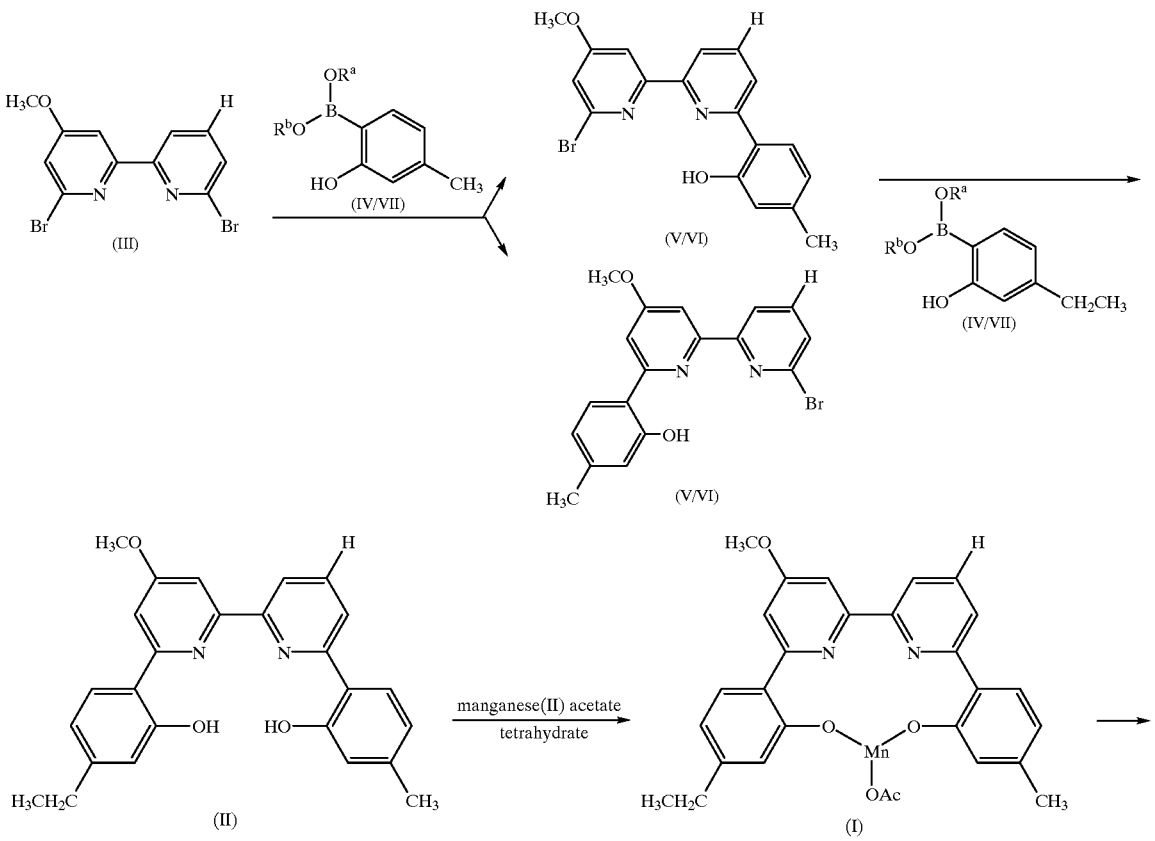

Scheme I
Synthesis of manganese (III) bipyridine derivatives

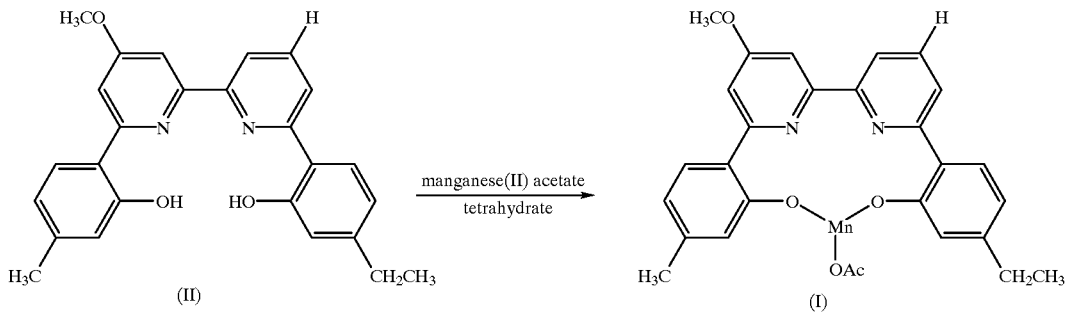

In Reaction Scheme 1, separation of the isomeric compounds of formulae (V/VI) could be carried out, for example by flash chromatography, prior to their subsequent reaction. Alternatively, the mixture of isomeric complexes of formula (I) could be separated, for example by HPLC. As a further alternative, the mixture of isomeric compounds of formula (II) could be separated prior to their subsequent complexation reaction (although this will in general be more difficult and thus less preferred, given their typical solubility characteristics).

The compounds of formulae (III), (IV) and (VII) referred to above are either readily available or may be readily synthesised by those skilled in the art using conventional methods of organic synthesis.

Reaction Schemes 2 and 3 below are representative illustrations of possible methods for the preparation of compounds of formula (III). Reagents and reaction conditions for the individual steps in these Schemes will be well-known to the person skilled in the art. The following references are particularly pertinent: Rodriguez-Ubis, J C et al. (1997) *Helv. Chim. Acta* 80: 86–96; Neumann U et al. (1989) *Chem. Ber.* 122: 589–591.

Reaction Scheme 2

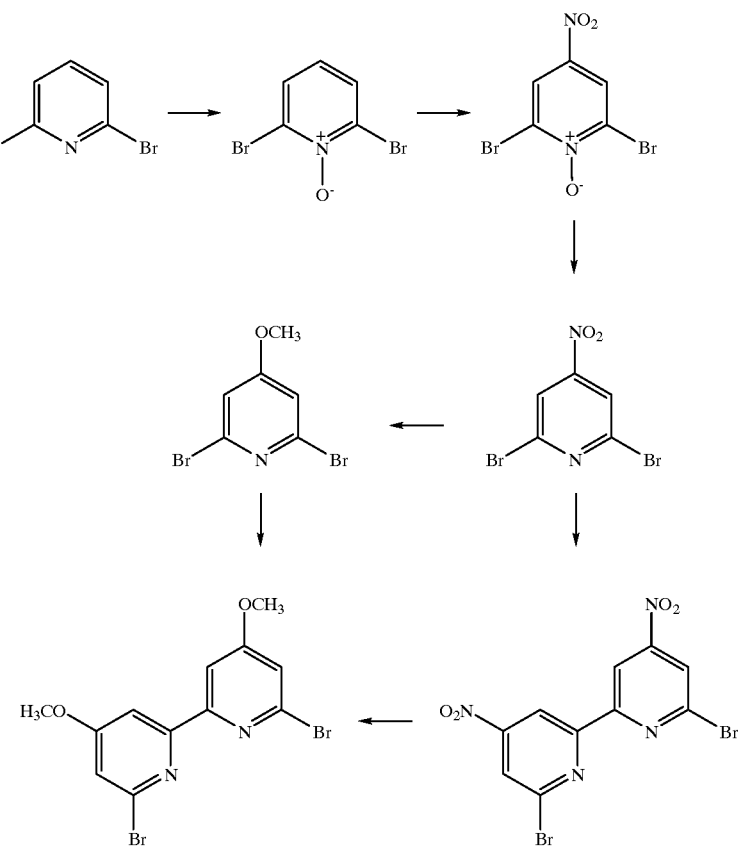

Reaction Scheme 3

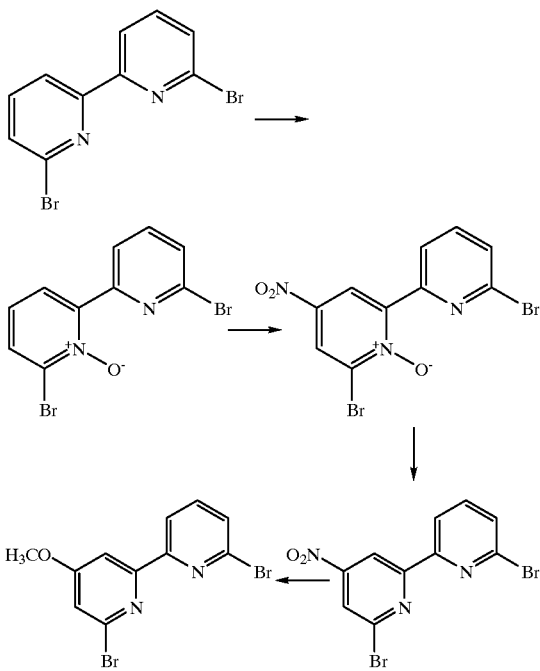

The compounds of formulae (IV) and (VII) are in general prepared by reaction of an appropriately protected phenol derivative with a borane reagent as illustrated in the general synthetic procedures and specific Examples described below.

Various intermediate compounds used in the above-mentioned processes, including but not limited to certain of the compounds of formulae (II), (III), (IV), (V), (VI) and (VII), as illustrated above, are novel and thus represent a further aspect of the present invention.

In particular, a further aspect of the present invention is intermediate compounds of formula (II) as defined above; with the exception of 6,6'-Bis(2-hydroxyphenyl)-2,2'-bipyridine.

A further aspect of the present invention is intermediate compounds of formula (III) as defined above; with the exception of 6,6'-dibromo-2,2'-bipyridyl and 6,6'-dibromo-4,4'-dimethoxy-2,2'-bipyridyl.

A further aspect of the present invention is intermediate compounds of formula (IV) or (VII) as defined above; with the exception of 2-hydroxyphenylboronic acid.

A further aspect of the present invention is intermediate compounds of formula (V) or (VI) as defined above.

Whilst it is possible for the compounds of the present invention to be administered as the complex per se, it is preferred to present them in the form of a pharmaceutical formulation.

Pharmaceutical formulations can be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations can be prepared by any method known in the art of pharmacy, for example by bringing into association the active ingredient with the carrier(s), diluent(s) or excipient(s).

Thus, according to a further aspect of the present invention there is provided a pharmaceutical formulation comprising at least one compound of formula (I) or a solvate thereof together with one or more pharmaceutically acceptable carriers, diluents or excipients.

Pharmaceutical formulations may be presented in unit dose forms containing a predetermined amount of active ingredient per unit dose. Such a unit may contain for example 1 μg to 10 g, preferably 0.01 mg to 1000 mg, more preferably 0.1 mg to 250 mg, of a compound of formula (I) or a solvate thereof, depending on the condition being treated, the route of administration and the age, weight and condition of the patient.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. Typically, tablet or capsules will be prepared to contain from 1 mg to 1000 mg, preferably 2.5 mg to 250 mg of active ingredient per unit dose.

Pharmaceutical formulations adapted for transdermal administration may be resented as discrete patches intended to remain in intimate contact with the pidermis of the recipient for a prolonged period of time. For example, the active ingredient may be delivered from the patch by iontophoresis as generally described in *Pharmaceutical Research*, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas; rectal ointments and foams may also be employed.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators. Spray compositions may, for example, be formulated as aerosols delivered from pressurised packs, such as a metered dose inhaler, with the use of a suitable liquified propellant. Capsules and cartridges for use in an inhaler or insufflator, of for example gelatine, may be formulated containing a powder mix for inhalation of a compound of the invention and a suitable powder base such as lactose or starch. Each capsule or cartridge may generally contain between 1 µg–10 mg of the compound of formula (I) or a solvate thereof. Aerosol formulations are preferably arranged so that each metered dose or "puff" of aerosol contains 1 µg–2000 µg, preferably about 1 µg–500µg of a compound of formula (I) or a solvate thereof. Administration may be once daily or several times daily, for example 2, 3, 4 or 8 times, giving for example 1, 2 or 3 doses each time. The overall daily dose with an aerosol will generally be within the range 10 µg–10 mg, preferably 100 µg–2000 µg. The overall daily dose and the metered dose delivered by capsules and cartridges in an inhaler or insufflator will generally be double those with aerosol formulations.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Further examples of suitable pharmaceutical formulations are given in the prior art patent documents referred to above, particularly in WO96/40149.

As used herein, an "antioxidant" is a substance that, when present in a mixture or structure containing an oxidizable substrate biological molecule, significantly delays or prevents oxidation of the substrate biological molecule. Antioxidants can act by scavenging biologically important reactive free radicals or other reactive oxygen species (•$O_2^-$, $H_2O_2$, •OH, HOCl, ferryl, peroxyl, peroxynitrite, and alkoxyl), or by preventing their formation, or by catalytically converting the free radical or other reactive oxygen species to a less reactive species. An antioxidant compound of the present invention generally has detectable SOD, CAT and/or POD activity. A compound of the present invention has antioxidant activity if the complex, when added to a cell culture or assay reaction, produces a detectable decrease in the amount of a free radical, such as superoxide, or a nonradical reactive oxygen species, such as hydrogen peroxide, as compared to a parallel cell culture or assay reaction that is not treated with the complex. The relative amount of free radical species is often determined by detection of a secondary indicator (e.g., an oxidized substrate; peroxidized lipid, cytochrome C).

As used herein, "free radical-associated diseases or conditions" refers to a pathological condition of an individual that results at least in part from the production of or exposure to free radicals, particularly oxyradicals, and other reactive oxygen species in vivo. It is evident to those of skill in the art that most pathological conditions are multifactorial, in that multiple factors contributing to the disease state are present, and that assigning or identifying the predominant causal factor(s) for any individual pathological condition is frequently extremely difficult.

For these reasons, the term "free radical associated disease" encompasses pathological states that are recognized in the art as being conditions wherein damage from free radicals or reactive oxygen species is believed to contribute to the pathology of the disease state, or wherein administration of a free radical inhibitor (e.g., desferrioxamine), scavenger (e.g., tocopherol, glutathione), or catalyst (e.g., SOD, catalase) is shown to produce a detectable benefit by decreasing symptoms, increasing survival, or providing other detectable clinical benefits in treating or preventing the pathological state. For example but not limitation, the disease states discussed herein are considered free radical-associated diseases (e.g., ischemic reperfusion injury, inflammatory diseases, systemic lupus erythematosus, myocardial infarction, stroke, traumatic hemorrhage, spinal cord trauma, Crohn's disease, autoimmune diseases (e.g., rheumatoid arthritis, diabetes), cataract formation, uveitis, emphysema, gastric ulcers, oxygen toxicity, neoplasia, undesired cell apoptosis, radiation sickness, and other pathological states discussed above, such as toxemia and acute lung injury). Such diseases can include "apoptosis-related ROS" which refers to reactive oxygen species (e.g., $O_2^-$, HOOH) which damage critical cellular components (e.g., lipid peroxidation) in cells stimulated to undergo apoptosis, such apoptosis-related ROS may be formed in a cell in response to an apoptotic stimulus and/or produced by non-respiratory electron transport chains (i.e., other than ROS produced by oxidative phosphorylation).

The compounds of formula (I) and solvates thereof have antioxidant and/or free radical scavenging properties as demonstrated hereinafter by their SOD, CAT or POD mimetic activity.

The present invention thus also provides compounds of formula (I) and solvates thereof for use in medical therapy. The compounds of the present invention are of potential utility in treating and preventing free radical associated diseases and conditions which involve a component of oxidative stress including, for example, Alzheimer's disease, dementia, Parkinson's disease, Lou Gehrig disease, motor neurone disorders, Huntington's disease, cancer, multiple sclerosis, systemic lupus erythematosus, scleroderma, eczema, dermatitis, delayed type hypersensitivity, psoriasis, gingivitis, adult respiratory distress syndrome, septic shock, multiple organ failure, asthma, allergic rhinitis, pneumonia, emphysema, chronic bronchitis, AIDS, inflammatory bowel disease, pancreatitis, transplantation rejection, atherosclerosis, hypertension, congestive heart failure, myocardial ischemic disorders, angioplasty, endocarditis, retinopathy of premanurity, cataract formation, uveitis, rheumatoid arthritis and osteoarthritis.

The compounds of formula (I) and solvates thereof are also of potential utility in treating and preventing free radical-associated diseases or conditions as referred to above.

In preferred embodiments, the compounds of the present invention and formulations thereof may used for preventing, arresting, or treating (1) neurological damage such as Parkinson's disease or Alzheimer's disease, (2) cardiac tissue necrosis resulting from cardiac ischemia, (3) autoimmune neurodegeneration (e.g., encephalomyelitis), (4) acute lung injury such as in sepsis and endotoxemia, and (5) neuronal damage resulting from ischemia (e.g., stroke, drowning, brain surgery) or trauma (e.g., concussion or cord shock).

The compounds of the present invention and formulations thereof may also have utility for the following additional indications: (1) for preventing ischemic/reoxygenatjon injury in a patient, (2) for preserving organs for transplant in an anoxic, hypoxic, or hyperoxic state prior to transplant, (3) for protecting normal tissues from free radical-induced damage consequent to exposure to ionizing radiation and/or chemotherapy, as with bleomycin, (4) for protecting cells and tissues from free radical-induced injury consequent to exposure to xenobiotic compounds which form free radicals, either directly or as a consequence of monooxygenation through the cytochrome P-450 system, (5) for enhancing cryopreservation of cells, tissues, organs, and organisms by increasing viability of recovered specimens and (6) for prophylactic administration to prevent carcinogenesis, cellular senescence, cataract formation, formation of malondialdehyde adducts, HIV pathology (as described below) and macromolecular crosslinking, such as collagen crosslinking.

The compounds of the present invention and formulations thereof may also be of benefit to patients who are infected with a human immunodeficiency virus (e.g., HIV-1) or who are at risk of becoming infected with a human immunodeficiency virus. The antioxidant compounds of the present invention may prevent or inhibit the induction of HIV-1 replication in CD4+ lymphocytes by tumor necrosis factor (TNF or other inflammatory mediators) and/or prevent damage to or death of CD4+ cells as a consequence of HIV-1 infection. Without wishing to be bound by any particular theory of HIV-1 replication or HIV-1 pathogenesis, it is believed that administration of an antioxidant complex can inhibit and/or slow the development of HIV-1 related pathology and/or can reduce the rate of decline of the CD4+ lymphocyte population in HIV infected individuals. The antioxidant compounds of the present invention may also inhibit pathology resulting from excessive or inappropriate levels of TNF or other inflammatory mediators, both in AIDS and in other conditions (e.g., septic shock). Frequently, a dosage of about 50 to 5000 mg will be administered to a patient with HIV and/or with excessive or inappropriate levels of TNF, either in single or multiple doses, to reduce or retard the development of pathology and clinical symptoms. Antioxidant compounds of the present invention may be administered therapeutically to treat viral diseases other than HIV.

The compounds of the present invention and formulations thereof may also have utility in enhancing the recovery of skin of a warm-blooded animal from wounds, such as surgical incisions, burns, inflammation or minor irritation due to oxidative damage, etc.

A further aspect of the invention provides a method of prophylaxis or treatment of a human or animal subject suffering from a diseases or condition which involves a component of oxidative stress and/or a free radical-associated disease or condition which comprises administering to said subject an effective amount of a compound of formula (I) or a solvate thereof.

A further aspect of the present invention provides the use of a compound of formula (I) or a solvate thereof in therapy.

A further aspect of the present invention provides the use of a compound of formula (I) or a solvate thereof in the preparation of a medicament for the prophylaxis or treatment of a disease or condition which involves a component of oxidative stress and/or a free radical-associated disease or condition.

A further aspect of the present invention provides the use of a compound of formula (I) or a solvate thereof in the preparation of a medicament for the prophylaxis or treatment of the specific disorders and conditions referred to above.

The compounds of the present invention and formulations thereof can be administered for prophylactic and/or therapeutic treatments. In therapeutic application, formulations are administered to a patient already affected by the particular free radical associated disease, in an amount sufficient to cure or at least partially arrest the condition and its complications. An amount adequate to accomplish this is defined as a "therapeutically effective dose" or "efficacious dose."

Amounts effective for this use will depend upon the severity of the condition, the general state of the patient, and the route of administration, but generally range from about 1 μg to about 10 g of antioxidant compounds of the present invention per dose, with dosages of from 0.1 mg to 2000 mg per patient being more commonly used.

In prophylactic applications, formulations containing the antioxidant compound of the present invention or cocktails thereof are administered to a patient not already in a disease state to enhance the patient's resistance or to retard the progression of disease. Such an amount is defined to be a "prophylactically effective dose." In this use, the precise amounts again depend upon the patient's state of health and general level of immunity, but generally range from 1 μg to 10 g per dose, especially 0.01 mg to 1000 mg per patient.

As indicated above, a typical formulation of a compound of the present invention will contain between about 0.1 and 250 mg of the complex in a unit dosage form. Single or multiple administrations of the formulations can be carried out with dose levels and dosing pattern being selected by the treating physician.

In general, for treatment of free radical-associated diseases, a suitable effective dose of the antioxidant compound of the present invention will be in the range of 0.01 micrograms (μg) to 1000 milligram (mg) per kilogram (kg) of body weight of recipient per day, preferably in the range of 0.1 μg to 100 mg per kg of body weight per day, more preferably in the range of 1 μg to 10 mg per kg of body weight per day. For example, 0.2 mg/kg for a 70 kg human adult would result in a daily dose of 14 mg. The desired dosage is preferably presented in one, two, three, four or more subdoses administered at appropriate intervals throughout the day. These subdoses can be administered as unit dosage forms as referred to above.

Kits can also be supplied for use with the compounds of the present invention for use in the protection against or therapy for a free radical-associated disease. Thus, the subject formulation of the present invention may be provided, usually in a lyophilized form or aqueous solution in a container, either alone or in conjunction with additional antioxidant compounds of the present invention of the desired type. The antioxidant compounds are included in the kits with buffers, such as Tris, phosphate, carbonate, etc., stabilizers, biocides, inert proteins, e.g. serum albumin, or the like, and a set of instructions for use. Generally, these materials will be present in less than about 5% wt. based on the amount of antioxidant compounds of the present invention and usually present in total amount of at least about 0.001% based again on the concentration. Frequently, it will be desirable to include an inert extender or excipient to dilute the active ingredients, where the excipient may be present in from about 1 to 99.999% wt. of the total formulation.

The compounds of the present invention may be employed alone or in combination with other therapeutic agents for the treatment of the above-mentioned conditions, and in particular in combination with other antioxidant agents that have SOD activity, catalase activity, peroxidase activity, or are free radical scavengers or inhibitors of free radical formation. Combination therapies according to the present invention thus comprise the administration of at least one compound of formula (I) or a pharmaceutically acceptable solvate thereof and at least one other pharmaceutically active agent. The compound(s) of formula (I) or a solvate thereof and the other pharmaceutically active agent(s) may be administered together or separately and, when administered separately this may occur simultaneously or sequentially in any order. The amounts of the compound(s) of formula (I) or a solvate thereof and the other pharmaceutically active agent(s) and the relative timings of administration will be selected in order to achieve the desired combined therapeutic effect.

Certain embodiments of the present invention will now be illustrated by way of example only. The physical data given for the compounds exemplified is consistent with the assigned structure of those compounds.

EXAMPLES

I. General Characterization Methods

A. Nuclear Magnetic Resonance (NMR)

$^1$H NMR spectra were obtained at 500 MHz on a Bruker AMX500 spectrophotometer, at 400 MHz on a Bruker DPX400, on a Bruker spectrophotometer at 300 MHz, or on a Bruker AC250 or Bruker AM250 spectrophotometer at 250 MHz. J values are given in Hz. Mass spectra were obtained on one of the following machines: VG Micromass Platform (electrospray positive or negative), HP5989A Engine (thermospray positive) or Finnigan-MAT LCQ (ion trap) mass spectrometer.

B. High Performance Liquid Chromatography (HPLC)

Where HPLC retention times are given as a characterization of intermediates or Examples these refer to the following two systems:

System 1: an HP 1100 platform series II running a 5.5 minute gradient.
    Eluents: A—0.1% v/v formic acid+10 mmol ammonium acetate
    B—95% MeCN+0.05% v/v formic acid
    Flow rate: 3 ml/min
    Column: 3 0.3 cm×4.6 mm internal diameter, 3 µm ABZ+PLUS
    Injection Volume: 5 µl
    Temperature: Room temperature.
    Gradient:

| Time: | % A | % B |
|---|---|---|
| 0.00 | 100 | 0.00 |
| 0.70 | 100 | 0.00 |
| 4.40 | 0.00 | 100 |
| 5.30 | 0.00 | 100 |
| 5.50 | 100 | 0.00 |

System 2: an HP1050 platform series II running an 8.0 minute gradient.
    Eluents: A—0.1% v/v formic acid+10 mmol ammonium acetate
    B—95% MeCN+0.05% v/v formic acid
    Flow rate: 1 ml/min
    Column: 3.3 cm×4.6 mm internal diameter, 3 µm ABZ+PLUS
    Injection Volume: 5 µl
    Temperature: Room temperature.
    Gradient:

| Time: | % A | % B |
|---|---|---|
| 0.00 | 100 | 0.00 |
| 0.70 | 100 | 0.00 |
| 4.20 | 0.00 | 100 |
| 7.70 | 0.00 | 100 |
| 8.00 | 100 | 0.00 |

Ether refers to diethylether.
DCM refers to dichloromethane
DMSO refers to dimethylsulphoxide.
DMF refers to dimethylformamide.
DME refers to 1,2-dimethoxyethane.
hexanes refers to the commonly sold mixture of hexane isomers.
THF refers to tetrahydrofuran.
MS refers to mass spectrum.

II. General Synthetic Procedures

A. Method of Preparing Bipyridine Derivatives

1) Preparation of Tetrahydropyran Protected Phenols

To a mixture of the appropriate phenol (36 mmol) and 3,4-dihydro-2H-pyran (5 ml, 55 mmol) stirring at room temperature under nitrogen was added a catalytic amount of picric acid. Stirring was continued for 24 hours. The reaction was diluted with 25 ml of cyclohexane and basic alumina (2 g) was added. This mixture was stirred for 10 minutes and then passed through a short column of basic alumina, eluting with cyclohexane. The combined filtrate and washings were concentrated under vacuum to give the desired protected phenol derivative, generally as an oil.

2) Preparation of Boronic Acid Derivatives

The tetrahydropyran-protected phenol (10.6 mmol) was dissolved in dry THF (40 ml) and the solution cooled to 0° C. n-Butyl lithium (1.6M in hexanes, 10 ml, 16 mmol) was added dropwise with stirring over 10 minutes. The ice-bath was removed and the reaction stirred at room temperature overnight. Triisopropoxy borane (3.5 ml, 15 mmol) was added and stirring continued for 24 hours. The reaction was quenched with water, acidified to pH 1 with 2N hydrochloric acid and extracted with ether (2×200 ml). The combined organic extracts were washed with 2N hydrochloric acid (50 ml), dried with magnesium sulphate and concentrated under vacuum. The oily solid generally produced was triturated with cyclohexane to give the desired boronic acid derivative, typically as an off-white solid.

3) Method 1: Preparation of Bipyridine Derivatives

A mixture of the boronic acid derivative (1.9 mmol), 6,6'-dibromo-2,2'-bipyridyl (260 mg, 0.82 mmol; Uchida Y et al. (1994) *Heteroatom. Chemistry* 5(4): 409–412), sodium carbonate (2N solution, 2 ml) and tetrakis (triphenylphosphine) palladium (50 mg) in propan-2-ol (10 ml) was heated at reflux under nitrogen for 8 hours. The reaction was diluted with water and the solid was filtered off and washed with water, to give the desired bipyridine derivative.

4) Method 2: Preparation of Bipyridine Derivatives 6,6'-Dibromo-2,2'-bipyridyl (5.0 g, 15.9 mmol) in propan-2-ol (500 ml) was heated to 100° C. with stirring. The boronic acid derivative (3.2 mmol), sodium carbonate (2N solution, 50 ml) and tetrakis(triphenylphosphine) palladium (100 mg) was added and the mixture heated at reflux under nitrogen for 2 hours. The cooled reaction was filtered and the filtrate was reduced to dryness under vacuum. The residue was washed with water and purified by column chromatography to give the desired product, generally as a yellow solid.

5) Method 3: Preparation of Bipyridine Derivatives

A mixture of the 6-Bromo-6'-(2-hydroxyphenyl)-2,2'-bipyridine derivative (0.14 mmol), the boronic acid derivative (0.16 mmol), sodium carbonate (2N solution, 0.5 ml) and tetrakis(triphenylphosphine) palladium (10 mg) in propan-2-ol (5 ml) was heated at reflux, under nitrogen for 18 hours. The cooled reaction was diluted with water and filtered. The residue was washed with water, dissolved in toluene and filtered through a short column of silica, eluting with further toluene. The combined filtrate and washings were reduced to dryness under vacuum to give the desired product.

B. Preparation of Manganese Bipyridine Complex

The ligand (0.38 mmol) and manganese (II) acetate tetrahydrate (93 mg, 0.38 mmol) were mixed in methanol (20 ml) and stirred at room temperature until no ligand remained. The solution was then filtered and reduced to dryness under vacuum. The brown residue generally obtained was triturated with acetone to give the desired final product.

C. Counter Ion Exchange

The appropriate acetate complex (0.0088 mmol) is dissolved in water (2 ml) and sodium chloride (17.5 mg, 0.3 mmol) is added. The corresponding chloride complex precipitates out over 10 minutes and is filtered off to give the product, generally as a brown solid.

D. Starting Materials and Intermediate Compounds

1) Preparation of 2-(2-Ethoxyphenoxy)tetrahydropyran 2-(2-Ethoxyphenoxy)tetrahydropyran was prepared in 95% yield from 2-ethoxyphenol using method A; δH [$^2$H]-CHCl$_3$ 7.13,(1H, d), 6.93,(3H, m), 5.40,(1H, t), 4.07,(3H, m), 3.60,(1H, m), 2.00–1.60,(6H, m), 1.44,(3H, t).

2) Preparation of 2-(2-Methoxy-4-methylphenoxy)tetrahydropyran 2-(2-Methoxy-4-methylphenoxy)tetrahydropyran was prepared in 95% yield from 2-methoxy-4-methylphenol using method A; δH [$^2$H$_6$]-DMSO 7.00,(1H, d), 6.85,(1H, s), 6.70,(1H, d), 5.85,(1H, t), 3.88,(1H, m), 3.80,(3H, s), 3.52, (1H, m), 2.29,(3H, s), 2.00–1.50,(6H, m).

3) Preparation of 2-(4-Fluoro-phenoxy)tetrahydropyran 2-(4-Fluoro-phenoxy)tetrahydropyran was prepared in quantitative yield from 4-fluorophenol using method A; δH [$^2$H$_6$]-DMSO 7.11,(3H, m), 5.45,(1H, s), 3.79,(1H, m), 3.60,(1H, m), 2.00–1.45,(6H, m).

4) Preparation of 2-(2,4-Dimethylphenoxy)tetrahydropyran 2-(2,4-Dimethylphenoxy)tetrahydropyran was prepared in 95% yield from 2,4-dimethylphenol using method A; δH [$^2$H$_6$]-DMSO 7.03,(1H, s), 6.98,(2H, s), 4.97,(1H, s), 3.81, (1H, m), 3.60,(1H, m), 2.25,(3H, s), 2.23,(3H, s), 2.06–1.50, (6H, m).

5) Preparation of 2-(2-Fluorophenoxy)tetrahydropyran 2-(2-Fluorophenoxy)tetrahydropyran was prepared in 99% yield from 2-fluorophenol using method A; δH [$^2$H$_6$]-DMSO 7.27,(1H, d), 7.19,(1H, d), 7.09,(1H, t), 6.99,(1H, m), 5.50,(1H, s), 3.78,(1H, m), 3.54,(1H, m), 1.90–1.47,(6H, m).

6) Preparation of 2-(2-Hexylphenoxy)tetrahydropyran 2-(2-Hexylphenoxy)tetrahydropyran was prepared in 94% yield from 2-hexylphenol using method A; δH [$^2$H]-CHCl$_3$ 7.18–7.05,(3H, m), 6.99,(1H, t), 5.42,(1H, t), 3.91, (1H, m), 3.63,(1H, m), 2.63,(2H, t), 1.89,(2H, m), 1.80–1.51,(6H, m), 1.46–1.21,(6H, m), 0.90,(3H, t).

7) Preparation of 2-(2,3-Dimethylphenoxy)tetrahydropyran 2-(2,3-Dimethylphenoxy)tetrahydropyran was prepared in 96% yield from 2,3-dimethylphenol using method A; δH [$^2$H]-CHCl$_3$ 7.03,(1H, t), 6.94,(1H, d), 6.80,(1H, d), 5.38, (1H, t), 3.91,(1H, m), 3.60,(1H, m), 2.28,(3H, s), 2.20,(3H, s), 1.88,(2H, m), 1.77–1.50,(4H, m).

8) Preparation of 2-(4-Ethylphenoxy)tetrahydropyran 2-(4-Ethylphenoxy)tetrahydropyran was prepared from 4-ethylphenol in 80% yield using method A; δH [$^2$H]-CHCl$_3$ 7.10,(2H, d), 6.98,(2H, d), 5.38,(1H, t), 3.94,(1H, m), 3.59, (1H, m), 2.60,(2H, q), 1.85,(2H, m), 1.75–1.50,(4H, m), 1.20,(3H, t).

9) Preparation of 2-(4-Isopropylphenoxy)tetrahydropyran 2-(4-Isopropylphenoxy)tetrahydropyran was prepared in 93% yield from 4-isopropylphenol using method A; δH [$^2$H]-CHCl$_3$ 7.12,(2H, d), 6.98,(2H, d), 5.38,(1H, t), 3.93, (1H, m), 3.59,(1H, m), 2.87,(1H, m), 1.95,(2H, m), 1.74–1.50,(4H, m), 1.21,(6H, d).

10) Preparation of 2-(3-Ethylphenoxy)tetrahydropyran 2-(3-Ethylphenoxy)tetrahydropyran was prepared in 88% yield from 3-ethylphenol using method A; δH [$^2$H]-CHCl$_3$ 7.20,(1H, t), 6.92–6.79,(3H, m), 5.40,(1H, t), 3.92,(1H, m), 3.59,(1H, m), 2.61,(2H, q), 1.85,(2H, m), 1.75–1.50,(4H, m), 1.21,(3H, t).

11) Preparation of 2-Hydroxy-5-methoxyphenylboronic acid 2-(2-Bromo-4-methoxyphenoxy)tetrahydropyran (1.9 g, 6.62 mmol) was dissolved in dry THF (25 ml) and the solution cooled to −78° C. under nitrogen. n-Butyl lithium (1.6M in hexanes, 4.6 ml, 7.36 mmol) was added dropwise with stirring over 10 minutes. The reaction was stirred at −78° C. for 1 hour. Triisopropoxy borane (1.6 ml, 6.9 mmol) was added dropwise and the mixture allowed to warm to room temperature overnight. The reaction was quenched with water, acidified to pH 1 with 2N hydrochloric acid and extracted with DCM (2×200 ml). The combined organic extracts were washed with 2N hydrochloric acid (50 ml), dried with magnesium sulphate and concentrated under vacuum. The oily solid produced was triturated with cyclohexane to give the title compound as a pale brown solid (660 mg, 59%); MS 166/167 (M-H)$^-$; HPLC retention time (system 2) 3.53 minutes.

12) Preparation of 2-Hydroxy-3-methoxyphenylboronic acid 2-Hydroxy-3-methoxyphenylboronic acid was prepared in 57% yield from 2-(2-methoxyphenoxy)tetrahydropyran using method B; MS 166/167 (M-H)$^-$; HPLC retention time (system 2) 3.36 minutes.

13) Preparation of 2-Hydroxy-3-ethoxyphenylboronic acid 2-Hydroxy-3-ethoxyphenylboronic acid was prepared in 24% yield from 2-(2-ethoxyphenoxy)tetrahydropyran using method B; MS 181 (M-H)$^-$; HPLC retention time (system 1) 2.45 minutes.

14) Preparation of 2-Hydroxy-3-methoxy-5-methylphenylboronic acid 2-Hydroxy-3-methoxy-5-methylphenylboronic acid was prepared in 60% yield from 2-(2-methoxy-4-methylphenoxy)tetrahydropyran using method B; MS 181(M-H)$^-$; HPLC retention time (system 1) 2.43 minutes.

15) Preparation of 5-Fluoro-2-hydroxyphenylboronic acid

5-Fluoro-2-hydroxyphenylboronic acid was prepared in 47% yield from 2-(4-fluorophenoxy)tetrahydropyran using method B; MS 155 (M-H)$^-$; HPLC retention time (system 1) 2.53 minutes.

16) Preparation of 2-Hydroxy-5-methylphenylboronic acid

2-Hydroxy-5-methylphenylboronic acid was prepared in 62% yield from 2-(4-methylphenoxy)tetrahydropyran using method B; MS 151 (M-H)$^-$; HPLC retention time (system 1) 2.57 minutes.

17) Preparation of 2-Hydroxy-3-methylphenylboronic acid

2-Hydroxy-3-methylphenylboronic acid was prepared in 37% yield from 2-(2-methylphenoxy)tetrahydropyran using method B; MS 151 (M-H)$^-$; HPLC retention time (system 1) 2.77 minutes.

18) Preparation of 2-Hydroxy-3,5-dimethylphenylboronic acid 2-Hydroxy-3,5-dimethylphenylboronic acid was prepared from 2-(2,4-dimethylphenoxy)tetrahydropyran in 40% yield using method B; MS 165 (M-H)$^-$; HPLC retention time (system 1) 2.94 minutes.

19) Preparation of 3-Fluoro-2-hydroxyphenylboronic acid 3-Fluoro-2-hydroxy phenylboronic acid was prepared in 60% yield from 2-(2-fluorophenoxy)tetrahydropyran using method B; MS 155 (M-H)⁻; HPLC retention time (system 1) 2.45 minutes.

20) Preparation of 2-Hydroxy-4-methylphenylboronic acid

2-Hydroxy-4-methylphenylboronic acid was prepared in 48% yield from 2-(3-methylphenoxy)tetrahydropyran using method B; MS 151 (M-H)⁻; HPLC retention time (system 1) 2.61 minutes.

21) Preparation of 2,4-Bis(2-hydroxy-6-methoxyphenyl)-<1,3,2,4>-dioxaboratane 2-(3-Methoxyphenoxy)tetrahydropyran (2.02 g, 10.51 mmol) was dissolved in dry THF (40 ml) and the solution cooled to 0° C. n-Butyl lithium (1.6M in hexanes, 10 ml, 16 mmol) was added dropwise with stirring over 10 minutes. The ice-bath was removed and the reaction stirred at room temperature overnight. Triisopropoxy borane (3.5 ml, 15 mmol) was added and stirring continued for 24 hours. The reaction was quenched with water, acidified to pH 1 with 2N hydrochloric acid and extracted with ether (2×200 ml). The combined organic extracts were washed with 2N hydrochloric acid (50 ml), dried with magnesium sulphate and concentrated under vacuum. The oily solid produced was redissolved in ethyl acetate/cyclohexane (1:1) and passed through a short silica gel column, the filtrate was concentrated under vacuum. The sticky solid was triturated with ether/cyclohexane and the solid filtered off to give the title compound as a beige solid (360 mg, 25%); MS 301 (MH)⁺; HPLC retention time (system 1) 2.49 minutes.

22) Preparation of 2-Hydroxy-5-t-butylphenylboronic acid 2-Hydroxy-5-t-butylphenylboronic acid was prepared from 2-(4-t-butylphenoxy)-tetrahydropyran using method B; MS 193 (M-H)⁻; HPLC retention time (system 2) 4.37 minutes.

23) Preparation of 5-Allyl-2-hydroxy-3-methoxyphenylboronic acid 2-(4-Allyl-2-methoxyphenoxy)tetrahydropyran (2.0 g, 8.05 mmol) was dissolved in dry THF (70 ml) and the solution cooled to −78° C. sec-Butyl lithium (1.3M in hexanes, 7.4 ml, 9.62 mmol) was added dropwise with stirring over 10 minutes, the reaction was stirred at −78° C. for 2 hours. Triisopropoxy borane (3.4 ml, 14.6 mmol) was added and stirring continued for 4hours at −78° C. The reaction was quenched with water, acidified to pH 1 with 2N hydrochloric acid and extracted with ether (2×200 ml). The combined extracts were dried with magnesium sulphate and concentrated under vacuum. The oily solid produced was triturated with cyclohexane and the solid filtered off to give the title compound (41%); MS 207 (M-H)⁻; HPLC retention time (system 1) 2.73 minutes.

24) Preparation of 3-Allyl-2-hydroxyphenylboronic acid 2-(2-allylphenoxy)tetrahydropyran (3.5 g, 16.03 mmol) was dissolved in dry THF (120 ml) and the solution cooled to −78° C. sec-Butyl lithium (1.3M in hexanes, 14.7 ml, 19.11 mmol) was added dropwise with stirring over 10 minutes, the reaction was stirred at −78° C. for 2 hours. Triisopropoxy borane (6.7 ml, 28.77 mmol) was added and stirring continued for 4 hours at −78° C. The reaction was quenched with water, acidified to pH 1 with 2N hydrochloric acid and extracted with ether (2×200 ml). The combined extracts were dried with magnesium sulphate and concentrated under vacuum. The oily solid produced was triturated with cyclohexane and the solid filtered off to give the title compound (600 mg, 21%); MS 177 (M-H)⁻; HPLC retention time (system 1) 3.09 minutes.

25) Preparation of 3-Hexyl-2-hydroxyphenylboronic acid 2-(2-Hexylphenoxy)tetrahydropyran (1.162 g, 4.43 mmol) was dissolved in dry THF (20 ml) and the solution cooled to 0° C. n-Butyl lithium (1.6M in hexanes, 4.15 ml, 6.64 mmol) was added dropwise with stirring over 10 minutes. The ice-bath was removed and the reaction stirred at room temperature overnight. Triisopropoxy borane (1.43 ml, 6.2 mmol) was added and stirring continued for 24 hours. The reaction was quenched with water, acidified to pH 1 with 2N hydrochloric acid and extracted with ether (20 ml). The combined organic extracts were washed with 2N hydrochloric acid (50 ml), dried with sodium sulphate and concentrated under vacuum. The oily solid produced was dissolved in ether (30 ml) and stirred with 2N hydrochloric acid (15 ml) for 1 hour. The organic phase was separated, dried with sodium sulphate and concentrated under vacuum. The residue was triturated with cyclohexane and the solid filtered off to give the title compound (260 mg, 26%); MS 221 (M-H)⁻.

26) Preparation of 3,4-Dimethyl-2-hydroxyphenylboronic acid 3,4-Dimethyl-2-hydroxyphenylboronic acid was prepared from 2-(2,3-dimethylphenoxy)tetrahydropyran using method B; MS 165 (M-H)⁻; HPLC retention time (system 1) 2.98 minutes.

27) Preparation of 5-Ethyl-2-hydroxyphenylboronic acid

5-Ethyl-2-hydroxyphenylboronic acid was prepared from 2-(4-ethylphenoxy)tetrahydropyran using method B; MS 165 (M-H)⁻; HPLC retention time (system 1) 2.83 minutes.

28) Preparation of 2-Hydroxy-5-isopropylphenylboronic acid

2-Hydroxy-5-isopropylphenylboronic acid was prepared from 2-(4-isopropylphenoxy)tetrahydropyran using method B; MS 179 (M-H)⁻; HPLC retention time (system 1) 2.94 minutes.

29) Preparation of 4-Ethyl-2-hydroxyphenylboronic acid

4-Ethyl-2-hydroxyphenylboronic acid was prepared from 2-(3-ethylphenoxy)tetrahydropyran using method B; MS 165 (M-H)⁻; HPLC retention time (system 1) 2.84 minutes.

30) Preparation of 6,6'-Bis(2-hydroxyphenyl)-2,2'-bipyridine 6,6'-Bis(2-hydroxyphenyl)-2,2'-bipyridine (*New J. Chem.* (1994), 18:519–524) was prepared in 75% yield from 2-hydroxyphenylboronic acid using method C; δH [²H₆]-DMSO 8.35,(2H, d), 8.29–8.08,(6H, m), 7.38,(2H, t), 7.00, (4H, m).

31) Preparation of 6,6'-Bis(2-hydroxy-5-methoxyphenyl)-2,2'-bipyridine 6,6'-Bis(2-hydroxy-5-methoxyphenyl)-2,2'-bipyridine was prepared by reaction of 2-hydroxy-5-methoxyphenylboronic acid (650 mg, 3.87 mmol) with 6,6-dibromo-2,2'-bipyridyl (520 mg, 1.64 mmol), sodium carbonate (2N solution, 4 ml) and tetrakis (triphenylphosphine) palladium (40 mg) in ethylene glycol dimethyl ether (16 ml) at reflux under nitrogen for 11 hours. The solid was filtered from the cooled reaction and washed with ether and water. The residue was dissolved in toluene and filtered through a short column of silica, washing through with further toluene. The combined filtrate and washings were concentrated under vacuum to give the desired product as a yellow solid (286 mg, 44%); δH [²H₆]-DMSO 8.30,(2H, d), 8.13,(4H, m), 7.56,(2H, s), 6.88, (4H, m), 3.73,(6H, s).

32) Preparation of 6,6'-Bis(2-hydroxy-3-methoxyphenyl)-2,2'-bipyridine 6,6'-Bis(2-hydroxy-3-methoxyphenyl)-2,2'-bipyridine was prepared in 58% yield from 2-hydroxy-3-methoxyphenylboronic acid using method C; δH [2H6]-DMSO 8.28,(2H, d), 8.16,(2H, t), 8.09,(2H, d), 7.63,(2H, d), 7.01,(2H, d), 6.85,(2H,t), 3.75,(6H, s).

33) Preparation of 6,6'-Bis(2-hydroxy-3-ethoxyphenyl)-2,2'-bipyridine 6,6'-Bis(2-hydroxy-3-ethoxyphenyl)-2,2'-bipyridine was prepared by reaction of 2-hydroxy-3-ethoxyphenylboronic acid (836 mg, 4.60 mmol) with 6,6-dibromo-2,2'-bipyridyl (722 mg, 2.30 mmol), sodium carbonate (2N solution, 6 ml) and tetrakis(triphenylphosphine) palladium (40 mg) in ethylene glycol dimethyl ether (30 ml) at reflux under nitrogen for 4 hours. The solid was filtered from the cooled reaction and washed with ether and water and toluene, to give the desired product as a yellow solid (446 mg, 48%);δH [$^2$H$_6$]-DMSO 8.33,(2H, d), 8.23,(2H, t), 8.14,(2H, d), 7.68,(2H, d), 7.05,(2H, d), 6.88,(2H, t), 4.06,(4H, q), 1.35,(6H, t).

34) Preparation of 6,6'-Bis(2-hydroxy-3-methoxy-5-methylphenyl)-2,2'-bipyridine 6,6'-Bis(2-hydroxy-3-methoxy-5-methylphenyl)-2,2'-bipyridine was prepared from 2-hydroxy-3-methoxy-5-methylphenylboronic acid in 83% yield using method C; δH [$^2$H$_6$]-DMSO 8.30,(2H, d), 8.22,(2H, t), 8.13,(2H, d), 7.53, (2H, s), 6.93,(2H, s), 3.82,(6H, s), 2.35,(6H, s).

35) Preparation of 6,6'-Bis(2-hydroxy-5-fluorophenyl)-2,2'-bipyridine 6,6'-Bis(2-hydroxy-5-fluorophenyl)-2,2'-bipyridine was prepared in 97% yield from 5-fluoro-2-hydroxyphenylboronic acid using method C; δH [$^2$H$_6$]-DMSO 8.55,(2H, d), 8.20,(4H, m), 8.00,(2h, dd), 7.15,(2H, dt), 6.98,(2H, m).

36) Preparation of 6,6'-Bis(2-hydroxy-5-methylphenyl)-2,2'-bipyridine 6,6'-Bis(2-hydroxy-5-methylphenyl)-2,2'-bipyridine was prepared in 73% yield from 2-hydroxy-5-methylphenylboronic acid using method C; δH [$^2$H$_6$]-DMSO 8.44,(2H, d), 8.32,(2H, t), 8.23,(2H, d), 8.05,(2H, s), 7.29,(2H, d), 7.00,(2H, d), 2.44,(6H, s).

37) Preparation of 6,6'-Bis(2-hydroxy-3-methylphenyl)-2,2'-bipyridine 6,6'-Bis(2-hydroxy-3-methylphenyl)-2,2'-bipyridine was prepared in 70% yield from 2-hydroxy-3-methylphenylboronic acid using method C; δH [$^2$H$_6$]-DMSO 8.35,(2H, d), 8.27,(2H, t), 8.07,(2H, d), 7.93,(2H, d), 7.24,(2H, d), 6.86,(2H, t), 2.20,(6H, s).

38) Preparation of Bis(2-hydroxy-3,5-dimethylphenyl)-2,2'-bipyridine

Bis(2-hydroxy-3,5-dimethylphenyl)-2,2'-bipyridine was prepared by reaction of 2-hydroxy-3,5-dimethylphenylboronic acid (321 mg, 1.92 mmol) with 6,6-dibromo-2,2'-bipyridyl (260 mg, 0.82 mmol), sodium carbonate (2N solution, 2 ml) and tetrakis (triphenylphosphine) palladium (20 mg) in ethylene glycol dimethyl ether (8 ml) at reflux under nitrogen for 88 hours. The solid was filtered from the cooled reaction and washed with acetone and water to give the desired product as a yellow solid (220 mg, 68%); δH [$^2$1H$_6$]-DMSO 8.39,(2H, d), 8.31,(2H, t), 8.10,(2H, 7.78,(2H, s), 7.10,(2H, s), 2.31, (6H, s), 2.24,(6H, s).

39) Preparation of 6,6'-Bis(2-hydroxy-3-fluorophenyl)-2,2'-bipyridine 6,6'-Bis(2-hydroxy-3-fluorophenyl)-2,2'-bipyridine was prepared by reaction of 3-fluoro-2-hydroxyphenylboronic acid (600 mg, 3.84 mmol) with 6,6-dibromo-2,2'-bipyridyl (520 mg, 1.64 mmol), sodium carbonate (2N solution, 4 ml) and tetrakis(triphenylphosphine) palladium (40 mg) in ethylene glycol dimethyl ether (16 ml) at reflux under nitrogen for 7 hours. The solid was filtered from the cooled reaction and washed with ethylene glycol dimethyl ether and water to give the desired product as a beige solid (240 mg, 39%); δH [$^2$H$_6$]-DMSO 8.49,(2H, d), 8.30,(4H, m), 8.00,(2H, d), 7.37, (2H, t), 6.99,(2H, dd).

40) Preparation of 6,6'-Bis(2-hydroxy-4-methylphenyl)-2,2'-bipyridine 6,6'-Bis(2-hydroxy-4-methylphenyl)-2,2'-bipyridine was prepared in 50% yield from 2-hydroxy-3-methylphenylboronic acid using method C; δH [$^2$H$_6$]-DMSO 8.25,(2H, d), 8.14,(2H, t), 8.02,(2H, d), 7.95,(2H, d), 6.75,(4H, m), 2.28,(6H, s).

41) Preparation of 6,6'-Bis(2,3-dihydroxyphenyl)-2,2'-bipyridine

To 6,6'-bis(2-hydroxy-3-methoxyphenyl)-2,2'-bipyridine (2.03 g, 50.8 mmol) dissolved in DCM (25 ml) was added boron tribromide (1M in DCM, 40.6 ml, 40.6 mmol) and the reaction stirred for 48 hours. The reaction was cooled to 0° C. and quenched by dropwise addition of methanol. The solvent was evaporated under vacuum to give the title compound as a yellow solid (100%); δH [$^2$H$_6$]-DMSO 8.30,(2H, d), 8.22,(2H, t), 8.10,(2H, d), 7.53,(2H, d), 6.88, (2H, d), 6.78,(2H, t).

42) Preparation of 6,6'-Bis(2-hydroxy-6-methoxyphenyl)-2,2'-bipyridine 2,4-bis(2-hydroxy-6-methoxyphenyl)-<1,3,2,4>-dioxaboratane (290 mg, 0.96 mmol)), 6,6-dibromo-2,2'-bipyridyl (260 mg, 0.82 mmol), sodium carbonate (2N solution, 2 ml) and tetrakis(triphenylphosphine) palladium (50 mg) in propan-2-ol (10 ml) was heated at reflux under nitrogen for 18 hours. The reaction was allowed to cool and the solid filtered off and washed with water and propan-2-ol, to give the title compound as a yellow solid (55 mg, 17%); δH-DMSO 8.11,(2H, d), 8.03,(2H, t), 7.91,(2H, d), 7.22, (2H, t), 6.60,(4H, m), 3.78,(6H, s); MS 401 (MH)$^+$.

43) Preparation of 6,6'-Bis(2-hydroxy-5-t-butylphenyl)-2,2'-bipyridine 6,6'-Bis(2-hydroxy-5-t-butylphenyl)-2,2'-bipyridine was prepared in 19% yield from 2-hydroxy-5-t-butylphenylboronic acid using method C; δH [$^2$H$_6$]-DMSO 8.48,(2H, d), 8.30,(4H, m), 8.14,(2H, s), 7.50,(2H, d), 7.03, (2H, d), 1.47,(16H, s).

44) Preparation of 6,6'-Bis(5-allyl-2-hydroxy-3-methoxyphenyl)-2,2'-bipyridine 6,6'-Bis(5-allyl-2-hydroxy-3-methoxyphenyl)-2,2'-bipyridine was prepared in 97% yield from 5-allyl-2-hydroxy-3-methoxyphenylboronic acid using method C; δH [$^2$H$_6$]-DMSO 8.46–8.10,(6H, m), 7.52,(2H, s), 6.92,(2H, s), 6.06,(2H, m), 5.11,(4H, m), 3.82,(6H, s), 3.44,(4H, d).

45) Preparation of 6-(2-Hydroxy-5-methoxyphenyl)-6'-(2-hydroxy-3-methylphenyl)-2,2'-bipyridine 6-(2-Hydroxy-5-methoxyphenyl)-6'-(2-hydroxy-3-methylphenyl)-2,2'-bipyridine was prepared from 6-bromo-6'-(2-hydroxy-5-methoxyphenyl)-2,2'-bipyridine and 2-hydroxy-3-methylphenylboronic acid in 65% yield using method F; δH [$^2$H$_6$]-DMSO 12.35,(1H, s), 8.37,(2H, m), 8.24,(2H, m), 8.17,(1H, d), 7.96,(1H, d), 7.65,(1H, s), 7.27, (1H, d), 7.02–6.86,(3H, m), 3.83,(3H, s), 8.09,(1H, s); MS 385 (MH)$^+$; HPLC retention time (system 1) 4.31 minutes.

46) Preparation of 6,6'-Bis(3-allyl-2-hydroxyphenyl)-2,2'-bipyridine 6,6'-Bis(3-allyl-2-hydroxyphenyl)-2,2'-bipyridine was prepared in 52% yield from 3-allyl-2-hydroxyphenylboronic acid using method C; δH [$^2$H$_6$]-DMSO 8.49,(2H, d), 8.31, (2H, t), 8.10,(2H, d), 8.00,(2H, d), 7.26,(2H, d), 6.95,(2H, t), 6.08,(2H, m), 5.06,(4H, m), 3.43,(4H, d).

47) Preparation of 6,6'-Bis(3-hexyl-2-hydroxyphenyl)-2,2'-bipyridine 6,6'-Bis(3-hexyl-2-hydroxyphenyl)-2,2'-bipyridine was prepared in 74% yield from 3-hexyl-2-hydroxyphenylboronic acid using method C; δH [$^2$H]-CHCl$_3$ 8.16,(2H, d), 8.03,(4H, m), 7.72,(2H, d), 7.22,(2H, d), 6.89,(2H, t), 2.75,(4H, t), 1.70,(4H, m), 1.50–1.26,(12H, m), 0.90,(6H, t).

48) Preparation of 6-Bromo-6'-(2-hydroxy-4-methylphenyl)-2,2'-bipyridine

6-Bromo-6'-(2-hydroxy-4-methylphenyl)-2,2'-bipyridine was prepared from 2-hydroxy-4-methylphenylboronic acid in 42% yield using method E; δH [$^2$H$_6$]-DMSO 13.38,(1H, b), 8.27,(1H, d), 8.20,(2H, d), 8.13,(1H, t), 8.05–7.96,(2H, m), 7.79,(1H, d), 6.79,(2h, m), 2.33,(3H, s).

49) Preparation of 6-(2-Hydroxyphenyl)-6'-(2-hydroxy-4-methylphenyl)-2,2'-bipyridine 6-(2-Hydroxyphenyl)-6'-(2-hydroxy-4-methylphenyl)-2,2'-bipyridine was prepared from 6-bromo-6'-(2-hydroxy-4-methylphenyl)-2,2'-bipyridine and 2-hydroxyphenylboronic acid in 68% yield using method F; δH [$^2$H$_6$]-DMSO 13.55, (1H, b), 13.39,(1H, b), 8.38–8.32,(4H, m), 8.30–8.20,(4H, m), 8.13,(3H, d), 8.03,(1H, d), 7.37,(1H, t), 7.00,(2H, m), 6.81,(2H, m), 2.30,(3H, s); MS 355 (MH)$^+$; HPLC retention time (system 1) 4.34 minutes.

50) Prepration of 6-(2-Hydroxy-3-methoxyphenyl)-6'-(2-hydroxy-4-methylphenyl)-2,2'-bipyridine 6-(2-Hydroxy-3-methoxyphenyl)-6'-(2-hydroxy-4-methylphenyl)-2,2'-bipyridine was prepared from 6-bromo-6'-(2-hydroxy-4-methylphenyl)-2,2'-bipyridine and 2-hydroxy-3-methoxyphenylboronic acid in 33% yield using method F; δH [$^2$H$_6$]-DMSO 13.52,(2H, b), 8.31,(2H, dd), 8.26,(1H, d), 8.21,(1H, d), 8.12,(1H, d), 8.02,(1H, d), 7.70,(1H, d), 7.09,(1H, d), 6.92, (1H, t), 6.82,(1H, d), 3.86,(3H, s), 2.32,(3H, s); MS 385 (MH)$^+$; HPLC retention time (system 1) 4.21 minutes.

51) Preparation of 6-(2-Hydroxy-5-methoxyphenyl)-6'-(2-hydroxy-4-methylphenyl)-2,2'-bipyridine 6-(2-Hydroxy-5-methoxyphenyl)-6'-(2-hydroxy-4-methylphenyl)-2,2'-bipyridine was prepared from 6-bromo-6'-(2-hydroxy-4-methylphenyl)-2,2'-bipyridine and 2-hydroxy-5-methoxyphenylboronic acid in 28% yield using method F; δH [$^2$H$_6$]-DMSO 13.70,(1H, b), 12.57,(1H, b), 8.38,(1H, d), 8.31,(1H, 8,25–8.17,(2H, m), 8.12,(1H, d), 8.02,(1H, d), 7.65,(1H, d), 7.00,(1H, dd), 6.94,(1H, d), 6.82,(2H, m), 3.82,(3H, s), 2.33,(3H, s); MS 385 (MH)$^+$; HPLC retention time (system 1) 4.28 minutes.

52) Preparation of 6-(2-Hydroxy-3-methylphenyl)-6'-(2-hydroxy-4-methylphenyl)-2,2'-bipyridine 6-(2-Hydroxy-3-methylphenyl)-6'-(2-hydroxy-4-methylphenyl)-2,2'-bipyridine was prepared from 6-bromo-6'-(2-hydroxy-4-methylphenyl)-2,2'-bipyridine and 2-hydroxy-3-methylphenylboronic acid in 84% yield using method F; δH [$^2$H$_6$]-DMSO 13.38,(1H, b), 8.41–8.22,(4H, m), 8.13,(1H, d), 8.09–8.01,(2H, m), 7.96,(1H, d), 7.28,(1H, d), 6.90,(1H, t), 6.80,(2H, m), 2.33,(3H, s), 2.26,(3H s); MS 369 (MH)$^+$; HPLC retention time (system 1) 4.53 minutes.

53) Preparation of 6-(3-Fluoro-2-hydroxyphenyl)-6'-(2-hydroxy-4-methylphenyl)-2,2'-bipyridine 6-(3-Fluoro-2-hydroxyphenyl)-6'-(2-hydroxy-4-methylphenyl)-2,2'-bipyridine was prepared from 6-bromo-6'-(2-hydroxy-4-methylphenyl)-2,2'-bipyridine and 3-fluoro-2-hydroxyphenylboronic acid in 17% yield using method F; δH [$^2$H$_6$]-DMSO 13.37,(1H, b), 8.38,(1H, d), 8.34–8.15,(4H, m), 8.10,(1H, d), 8.01,(1H, d), 7.95,(1H, d), 7.34,(1H, t), 6.98,(1H, m), 6.81,(2H, m), 2.33,(3H, s).

54) Preparation of 6-(3,4-Dimethyl-2-hydroxyphenyl)-6'-(2-hydroxy-4-methylphenyl)-2,2'-bipyridine 6-(3,4-Dimethyl-2-hydroxyphenyl)-6'-(2-hydroxy-4-methylphenyl)-2,2'-bipyridine was prepared from 6-bromo-6'-(2-hydroxy-4-methylphenyl)-2,2'-bipyridine and 3,4-dimethyl-2-hydroxyphenylboronic acid in 54% yield using method F; δH [$^2$H$_6$]-DMSO 13.40,(1H, b), 8.32,(2H, d), 8.24,(2H, m), 8.14–8.00,(3H, m), 7.86,(1H, d), 6.81,(3H, m), 2.33,(3H, s), 2.30,(3H, s), 2.19,(3H, s).

55) Preparation of 6-(2-Hydroxy-4-methylphenyl)-6'-(2-hydroxy-5-methylphenyl)-2,2'-bipyridine 6-(2-Hydroxy-4-methylphenyl)-6'-(2-hydroxy-5-methylphenyl)-2,2'-bipyridine was prepared from 6-bromo-6'-(2-hydroxy-4-methylphenyl)-2,2'-bipyridine and 5-methyl-2-hydroxyphenylboronic acid in 44% yield using method F; δH [$^2$H$_6$]-DMSO 13.60,(1H, b), 13.10,(1H, b), 8.32,(2H, t), 8.23,(2H, m), 8.13,(2H, d), 8.03,(1H, d), 7.95, (1H, s), 7.18,(1H, d), 6.92,(1H, d), 6.83,(2H, m), 2.33,(3H, s), 2.34,(3H, s); MS 369 (MH)$^+$; HPLC retention time (system 1) 4.46 minutes.

56) Preparation of 6-Bromo-6'-(2-hydroxy-3-methoxyphenyl)-2,2'-bipyridine

6-Bromo-6'-(2-hydroxy-3-methoxyphenyl)-2,2'-bipyridine was prepared from 2-hydroxy-3-methoxyphenylboronic acid in 38% yield using method E; δH [$^2$H$_6$]-DMSO 13.60,(1H, s), 8.29,(1H, d), 8.24,(2H, d), 8.06,(1H, t), 8.02,(1H, t), 7.80,(1H, d), 7.67,(1H, d), 7.08, (1H, d), 6.91,(1H, t), 3.84,(3H, s).

57) Preparation of 6-(2-Hydroxyphenyl)-6'-(2-hydroxy-3-methoxyphenyl)-2,2'-bipyridine 6-(2-Hydroxyphenyl)-6'-(2-hydroxy-3-methoxyphenyl)-2,2'-bipyridine was prepared from 6-bromo-6'-(2-hydroxy-3-methoxyphenyl)-2,2'-bipyridine and 2-hydroxyphenyl boronic acid in 39% yield using method F; δH [$^2$H$_6$]-DMSO 13.48,(1H, b), 13.38,(1H, b), 8.33,(2H, m), 8.23, (2H, t), 8.17,(2H, d), 8.13,(1H, d), 7.70,(2H, d), 7.37,(1H, t), 7.09, (1H, d), 7.02,(1H, d), 6.94,(1H, t), 3.84,(3H, s); MS 371 (MH)$^+$; HPLC retention time (system 1) 4.03 minutes.

58) Preparation of 6-(2-Hydroxy-3-methoxyphenyl)-6'-(2-hydroxy-5-methoxyphenyl)-2,2'-bipyridine 6-(2-Hydroxy-3-methoxyphenyl)-6'-(2-hydroxy-5-methoxyphenyl)-2,2'-bipyridine was prepared from 6-bromo-6'-(2-hydroxy-3-methoxyphenyl)-2,2'-bipyridine and 2-hydroxy-5-methoxyphenylboronic acid in 16% yield using method F; δH [$^2$H$_6$]-DMSO 13.72,(1H, b), 12.48,(1H, b), 8.39,(1H, d), 8.32,(1H, d), 8,27–8.14,(4H, m), 7.72,(1H, d), 7.67,(1H, s), 7.09,(1H, d), 7.04–6.90,(3H, m), 3.86,(6H, s); MS 401 (MH)$^+$; HPLC retention time (system 1) 3.98 minutes.

59) Preparation of 6-(2-Hydroxy-3-methoxyphenyl)-6'-(2-hydroxy-3-methylphenyl)-2,2'-bipyridine 6-(2-Hydroxy-3-methoxyphenyl)-6'-(2-hydroxy-3-methylphenyl)-2,2'-bipyridine was prepared from 6-bromo-6'-(2-hydroxy-3-methoxyphenyl)-2,2'-bipyridine and 2-hydroxy-3-methylphenylboronic acid in 59% yield using method F; δH [$^2$H$_6$]-DMSO 13.28,(1H, s), 8.37,(1H, d), 8.35,(1H, d), 8.29,(2H, t), 8.18,(1H, d), 8.10,(1H, d), 7.97, (1H, d), 7.71,(1H, d), 7.29,(1H, d), 7.10,(1H, d), 6.97–6.87, (2H, m), 3.84,(3H, s), 2.29,(3H, s); MS 385 (MH)$^+$; HPLC retention time (system 1) 4.27 minutes.

60) Preparation of 6-(2-Hydroxy-3-hexylphenyl)-6'-(2-hydroxy-3-methoxyphenyl)-2,2'-bipyridine 6-(2-Hydroxy-3-hexylphenyl)-6'-(2-hydroxy-3-methoxyphenyl)-2,2'-bipyridine was prepared from 6-bromo-6'-(2-hydroxy-3-methoxyphenyl)-2,2'-bipyridine and 2-hydroxy-3-hexylphenylboronic acid in 68% yield using method F; δH [$^2$H$_6$]-DMSO 13.23,(1H, s), 8.35,(2H, t), 8.27,(2H, m), 8.17,(1H, d), 8.10,(1H, d), 7.97,(1H, d), 7.72,(1H, d), 7.26,(1H, d), 7.09,(1H, d), 6.93,(2H, m), 3.84,(3H, s), 2.68,(2H, t), 1.62,(2H, m), 1.42–1.25(6H, m), 0.88(3H, t); MS 455 (MH)$^+$; HPLC retention time (system 1) 4.94 minutes.

61) Preparation of 6-(3,4-Dimethyl-2-hydroxyphenyl)-6'-(2-hydroxy-3-methoxyphenyl)-2,2'-bipyridine 6-(3,4-Dimethyl-2-hydroxyphenyl)-6'-(2-hydroxy-3-methoxyphenyl)-2,2'-bipyridine was prepared from 6-bromo-6'-(2-hydroxy-3-methoxyphenyl)-2,2'-bipyridine and 3,4-dimethyl-2-hydroxyphenylboronic acid in 11% yield using method F; δH [$^2$H$_6$]-DMSO 13.32,(1H, s), 8.38–8.22,(4H, m), 8.14,(1H, d), 8.10,(1H, d), 7.88,(1H, d), 7.72,(1H, d), 7.10,(1H, d), 6.94,(1H, t), 6.82,(1H, d), 3.84, (3H, s), 2.31,(3H, s), 2.20,(3H, s); MS 339 (MH)$^+$; HPLC retention time (system 1) 4.39 minutes.

62) Preparation of 6-(2-Hydroxy-3-methoxyphenyl)-6'-(2-hydroxy-5-methylphenyl)-2,2'-bipyridine 6-(2-Hydroxy-3-methoxyphenyl)-6'-(2-hydroxy-5-methylphenyl)-2,2'-bipyridine was prepared from 6-bromo-6'-(2-hydroxy-3-methoxyphenyl)-2,2'-bipyridine and 2-hydroxy-5-methylphenylboronic acid in 20% yield using method F; δH [$^2$H$_6$]-DMSO 13.57,(1H, b), 13.09,(1H, b), 8.33,(2H, t), 8.24,(2H, m), 8.15,(2H, m), 7.95,(1H, s), 7.70, (1H, d), 7.18,(1H, d), 7.10,(1H, d), 6.91,(2H, m), 3.84,)3H, s), 2.35,(3H, s); MS 385 (MH)$^+$; HPLC retention time (system 1) 4.17 minutes.

63) Preparation of 6-Bromo-6'-(2-hydroxy-5-methoxyphenyl)-2,2'-bipyridine

6-Bromo-6'-(2-hydroxy-5-methoxyphenyl)-2,2'-bipyridine was prepared from 2-hydroxy-5-methoxyphenylboronic acid in 39% yield using method E; δH [$^2$H$_6$]-DMSO 12.88,(1H, b), 8.34,(1H, d), 8.23,(2H, d), 8.15,(1H, t), 8.00,(1H, t), 7.80,(1H, t), 7.59,(1H, s), 7.00, (1H, d), 6.93,(1H, d), 3.81,(3H, s).

64) Preparation of 6-(2-Hydroxyphenyl)-6'-(2-hydroxy-5-methoxyphenyl)-2,2'-bipyridine 6-(2-Hydroxyphenyl)-6'-(2-hydroxy-5-methoxyphenyl)-2,2'-bipyridine was prepared from 6-bromo-6'-(2-hydroxy-5-methoxyphenyl)-2,2'-bipyridine and 2-hydroxyphenylboronic acid in 66% yield using method F; δH [$^2$H$_6$]-DMSO 13.55,(1H, s), 12.57,(1H, s), 8.35,(2H, m), 8.27–8.10,(5H, m), 7.65,(1H, s), 7.37,(1H, t), 7.03–6.93, (4H, m), 3.83,(3H, s); MS 371 (MH)$^+$; HPLC retention time (system 1) 4.08 minutes.

65) Preparation of 6-(3-Hexyl-2-hydroxyphenyl)-6'-(2-hydroxy-5-methoxyphenyl)-2,2'-bipyridine 6-(3-Hexyl-2-hydroxyphenyl)-6'-(2-hydroxy-5-methoxyphenyl)-2,2'-bipyridine was prepared from 6-bromo-6'-(2-hydroxy-5-methoxyphenyl)-2,2'-bipyridine and 3-hexyl-2-hydroxyphenylboronic acid in 57% yield using method F; δH [$^2$H$_6$]-DMSO 12.40,(1H, s), 8.36,(2H, m), 8.25,(2H, t), 8.18,(1H, d), 8.09,(1H, d), 7.96,(1H, d), 7.65,(1H, s), 7.25,(1H, d), 6.99,(1H, d), 6.96–6.8,(2H, m), 3.81,(3H, s), 2.67,(2H, t), 1.60,(2H, m), 1.42–1.25,(6H, m), 0.88,(3H, t); MS 455 (MH)$^+$; HPLC retention time (system 1) 4.96 minutes.

66) Preparation of 6-(3-Hexyl-2-hydroxyphenyl)-6'-(2-hydroxy-5-methoxyphenyl)-2,2'-bipyridine 6-(3,4-Dimethyl-2-hydroxyphenyl)-6'-(2-hydroxy-5-methoxyphenyl)-2,2'-bipyridine was prepared from 6-bromo-6'-(2-hydroxy-5-methoxyphenyl)-2,2'-bipyridine and 3,4-dimethyl-2-hydroxyphenylboronic acid in 50% yield using method F; δH [$^2$H$_6$]-DMSO 12.40,(1H, b), 8.38,(1H, d), 8.31,(1H, d), 8.28–8.20,(2H, m), 8.14,(1H, d), 8.09,(1H, d), 7.86,(1H, d), 7.66,(1H, s), 7.00,(1H, d), 6.94, (1H, d), 6.81,(1H, d), 3.82,(3H, s), 2.30,(3H, s), 2.19,(3H, s).

67) Preparation of 6-(5-Fluoro-2-hydroxyphenyl)-6'-(2-hydroxy-5-methoxyphenyl)-2,2'-bipyridine 6-(5-Fluoro-2-hydroxyphenyl)-6'-(2-hydroxy-5-methoxyphenyl)-2,2'-bipyridine was prepared from 6-bromo-6'-(2-hydroxy-5-methoxyphenyl)-2,2'-bipyridine and 5-fluoro-2-hydroxyphenylboronic acid in 50% yield using method F; δH [$^2$H$_6$]-DMSO 13.09,(1H, b), 12.63,(1H, b), 8.36,(2H, m), 8.22,(4H, m), 7,99,(1H, d), 7.64,(1H, s), 7.22,(1H, t), 7.05–6.91,(3H, m), 3.80,(3H, s).

68) Preparation of 6-(2-Hydroxy-5-methoxyphenyl)-6'-(2-hydroxy-5-methylphenyl)-2,2'-bipyridine 6-(2-Hydroxy-5-methoxyphenyl)-6'-(2-hydroxy-5-methylphenyl)-2,2'-bipyridine was prepared from 6-bromo-6'-(2-hydroxy-5-methoxyphenyl)-2,2'-bipyridine and 2-hydroxy-5-methylphenylboronic acid in 50% yield using method F; δH [$^2$H$_6$]-DMSO 13.27,(1H, b), 12.64,(1H, b), 8.37,(1H, d), 8.33,(1H, d), 8.21,(2H, t), 8.14,(2H, d), 7.93, (1H, s), 7.64,(1H, s), 7.17,(1H, d), 7.00,(1H, d), 6.93,(1H, d), 6.89,(1H, d), 3.82,(3H, s), 2.34,(3H, s).

69) Preparation of 6-(2-Hydroxy-5-methoxyphenyl)-6'-(2-hydroxy-3-methoxy-5-methylphenyl)-2,2'-bipyridine 6-(2-Hydroxy-5-methoxyphenyl)-6'-(2-hydroxy-3-methoxy-5-methylphenyl)-2,2'-bipyridine was prepared from 6-bromo-6'-(2-hydroxy-5-methoxyphenyl)-2,2'-bipyridine and 2-hydroxy-3-methoxy-5-methylphenylboronic acid in 43% yield using method F; δH [$^2$H$_6$]-DMSO 13.40,(1H, s), 12.51,(1H, s), 8.37,(1H, d), 8.29,(1H, d), 8.20,(2H, t), 8.14,(2H, d), 7.67,(1H, s), 7.51, (1H, s), 7.00,(1H, d), 6.94,(2H, m), 3.83,(6H, s), 2.34,(3H, s).

70) Preparation of 6-(2-Hydroxy-5-methoxyphenyl)-6'-(5-allyl-2-hydroxy-3-methoxyphenyl)-2,2'-bipyridine 6-(2-Hydroxy-5-methoxyphenyl)-6'-(5-allyl-2-hydroxy-3-methoxyphenyl)-2,2'-bipyridine was prepared from 6-bromo-6'-(2-hydroxy-5-methoxyphenyl)-2,2'-bipyridine and 5-allyl-2-hydroxy-3-methoxyphenylboronic acid in 42% yield using method F; δH [$^2$H$_6$]-DMSO 13.41,(1H, s), 12.52,(1H, s), 8.38,(1H, d), 8.27,(1H, d), 8.24–8.12,(4H, m), 7.65,(1H, s), 7.52,(1H, s), 6.99,(1H, d), 6.93,(2H, m), 6.05, (1H, m), 5.14,(1h, d), 5.07,(1H, d), 3.83,(6H, s), 3.40,(2H, d).

71) Preparation of 6-(2-Hydroxy-3-methoxyphenyl)-6'-(5-allyl-2-hydroxy-3-methoxyphenyl)-2,2'-bipyridine 6-(2-Hydroxy-3-methoxyphenyl)-6'-(5-allyl-2-hydroxy-3-methoxyphenyl)-2,2'-bipyridine was prepared from 6-bromo-6'-(2-hydroxy-3-methoxyphenyl)-2,2'-bipyridine and 5-allyl-2-hydroxy-3-methoxyphenylboronic acid in 37% yield using method F; δH [$^2$H$_6$]-DMSO 13.53,(1H, s), 13.31,(1H, s), 8.35–8.20,(4H, m), 8.16,(2H, d), 7.70,(1H, s), 7.53,(1H, s), 7.09,(1H, d), 6.93,(2H, m), 6.05,(1H, m), 5.14,(1h, d), 5.06,(1H, d), 3.85,(6H, s), 3.40,(2H, d).

72) Preparation of 6,6'-Bis(5-ethyl-2-hydroxyphenyl)-2,2'-bipyridine 6,6'-Bis(5-ethyl-2-hydroxyphenyl)-2,2'-bipyridine was prepared in 98% yield from 5-ethyl-2-hydroxyphenylboronic acid using method C; δH [$^2$H$_6$]-DMSO 8.36,(2H, d), 8.21,(2H, t), 8.13,(2H, d), 7.94,(2H, s), 7.20,(2H, d), 6.91,(2H, d), 2.62,(4H, q), 1.23,(6H, t); MS 397 (MH)$^+$; HPLC retention time (system 1) 4.59 minutes.

73) Preparation of 6,6'-Bis(2-hydroxy-5-isopropylphenyl)-2,2'-bipyridine 6,6'-Bis(2-hydroxy-5-isopropylphenyl)-2,2'-bipyridine was prepared in 90% yield from 2-hydroxy-5-isopropylphenylboronic acid using method C; δH [$^2$H$_6$]-DMSO 13.12,(2H, s), 8.36,(2H, d), 8.22,(2H, t), 8.13,(2H, d), 7.95,(2H, s), 7.25,(2H, d), 6.92,(2H, d), 2.95,(2H, m), 1.27,(12H, d).

74) Preparation of 6,6'-Bis(4-ethyl-2-hydroxyphenyl)-2,2'-bipyridine 6,6'-Bis(4-ethyl-2-hydroxyphenyl)-2,2'-bipyridine was prepared in 94% yield from 4-ethyl-2-hydroxyphenylboronic acid using method C; δH [$^2$H$_6$]-DMSO 8.33–7.96,(8H, m), 6.84,(4H, m), 2.60,(4H, q), 1.21, (6H, t).

EXAMPLES

Example 1

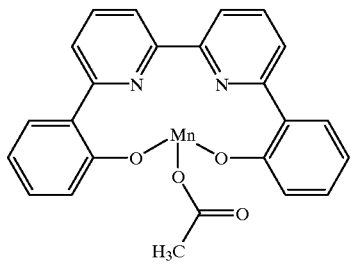

6,6'-Bis(2-hydroxyphenyl)-2,2'-bipyridine-manganese (III) acetate complex was prepared in 90% yield from 6,6'-bis (2-hydroxyphenyl)-2,2'-bipyridine using method D; δH [$^2$H$_4$]-MeOH includes: −25,(2H, b), 12,(2H, b), −1,(2H, b), −11.5,(2H, b), −12,(2H, b), −20,(2H, b), −42.5,(2H, b); MS 393 (M-OAc)$^+$; HPLC retention time (system 1) 2.38 minutes.

Example 2

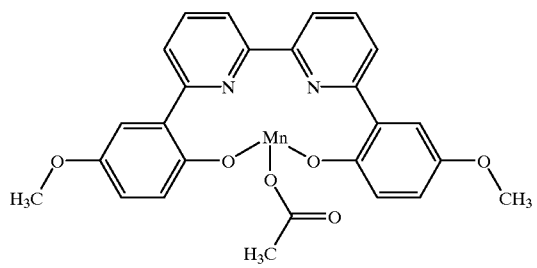

6,6'-Bis(2-hydroxy-5-methoxyphenyl)-2,2'-bipyridine (280 mg, 0.70 mmol) and manganese (II) acetate tetrahydrate (188 mg, 0.77 mmol) were mixed in ethanol (14 ml) plus a few drops of water and stirred at room temperature until no ligand remained. The solution was evaporated to dryness under vacuum. The brown residue was triturated with acetone to give 6,6'-bis(2-hydroxy-5-methoxyphenyl)-2,2'-bipyridine-manganese (III) acetate complex as a brown solid (285 mg, 80%); δH [$^2$H$_4$]-MeOH includes: −26,(2H, b), 8.5,(2H, b), 1.5,(6H, b), 0,(2H, b), −8,(2H, b), 18,(2H, b), −43,(2H, b). MS 453 (M-OAc)$^+$; HPLC retention time (system 2) 4.00 minutes.

Example 3

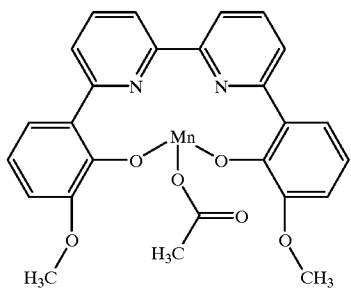

6,6'-Bis(2-hydroxy-3-methoxyphenyl)-2,2'-bipyridine (580 mg, 1.45 mmol) and manganese (II) acetate tetrahydrate (389 mg, 1.59 mmol) were mixed in ethanol (29 ml) plus a few drops of water and stirred at room temperature until no ligand remained. The solution was reduced to dryness under vacuum. The brown residue was triturated with acetone and the solid recrystallised from methanol/ether to give 6,6'-bis (2-hydroxy-3-methoxyphenyl)-2,2'-bipyridine-manganese (III) acetate complex as a black solid (250 mg, 34%); δH [$^2$H$_4$]-MeOH includes: −25.5,(2H, b), 11,(2H, b), 3.5,(6H, b), −6.5,(2H, b), −15,(2H, b), −20,(2H, b), −42.5,(2H, b); MS 453 (M-OAc)$^+$; HPLC retention time (system 1) 2.38 minutes.

Example 4

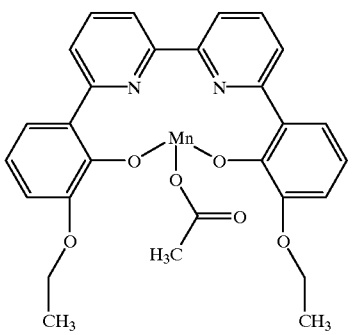

6,6'-Bis(2-hydroxy-3-ethoxyphenyl)-2,2'-bipyridine (75 mg, 0.17 mmol) and manganese (II) acetate tetrahydrate (46 mg, 0.19 mmol) were mixed in ethanol (7 ml) plus water (3 ml) and stirred at room temperature until no ligand remained. The solution was reduced to dryness under vacuum. The green residue was triturated with acetone to give 6,6'-bis(2-hydroxy-3-ethoxyphenyl)-2,2'-bipyridine-manganese (III) acetate complex as a dark green solid; MS 481 (M-OAc)$^+$; HPLC retention time (system 1) 2.62 minutes.

Example 5

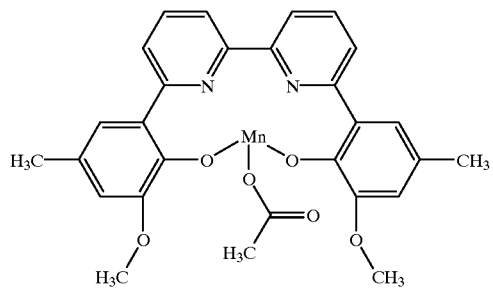

6,6'-Bis(2-hydroxy-3-methoxy-5-methylphenyl)-2,2'-bipyridine-manganese (III) acetate complex was prepared in 83% yield from 6,6'-bis(2-hydroxy-3-methoxy-5-methylphenyl)-2,2'-bipyridine using method D; δH [$^2$H$_4$]-MeOH includes: −26.5,(2H, b), 11.5,(6H, b), 9.5,(2H, b), 3.5,(6H, b), −11.8,(2H,b), −19.5,(2H, b), −43,(2H, b); MS 481 (M-OAc)$^+$; HPLC retention time (system 1) 2.53 minutes.

Example 6

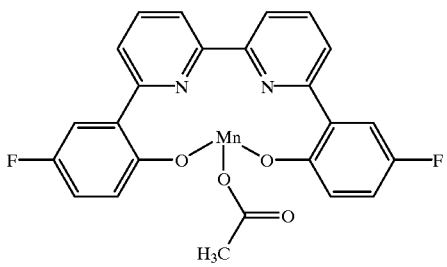

6,6'-Bis(2-hydroxy-5-fluorophenyl)-2,2'-bipyridine-manganese (III) acetate complex was prepared in 84% yield from 6,6'-bis(2-hydroxy-5-fluorophenyl)-2,2'-bipyridine using method D; δH [$^2$H$_4$]-MeOH includes: −25,(2H, b), 11,(2H, b), −0.3,(2H, b), −8,(2H,b), −19.5,(2H, b), −43.5, (2H, b); MS 429 (M-OAc)$^+$; HPLC retention time (system 1) 2.43 minutes.

Example 7

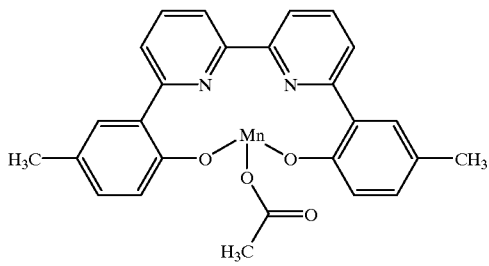

6,6'-Bis(2-hydroxy-5-methylphenyl)-2,2'-bipyridine-manganese (III) acetate complex was prepared in 91% yield from 6,6'-bis(2-hydroxy-5-methylphenyl)-2,2'-bipyridine using method D; δH [$^2$H$_4$]-MeOHincludes: −25.5,(2H, b), 16.5,(6H, b), −1,(2H, b), −0.5,(2H, b), −13,(2H, b), −19.5, (2H, b), −43,(2H, b); MS 421 (M-OAc)$^+$; HPLC retention time (system 1) 2.67 minutes.

Example 8

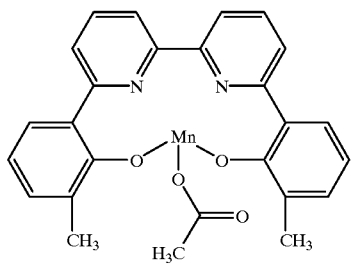

6,6'-Bis(2-hydroxy-3-methylphenyl)-2,2'-bipyridine-manganese (III) acetate complex was prepared in 83% yield from 6,6'-bis(2-hydroxy-3-methylphenyl)-2,2'-bipyridine using method D; δH [$^2$H$_4$]-MeOH includes: −27,(2H, b), 16,(6H, b), 13,(2H, b), −7.5,(2H, b), −16,(2H, b), −20,(2H, b), −43,(2H, b); MS 421 (M-OAc)$^+$; HPLC retention time (system 1) 3.15 minutes.

Example 9

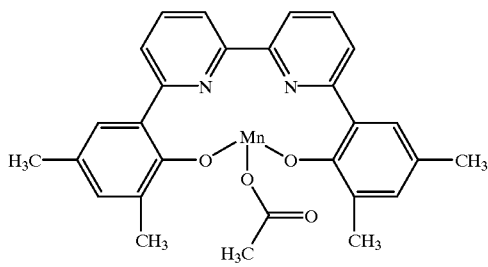

6,6'-Bis(2-hydroxy-3,5-dimethylphenyl)-2,2'-bipyridine-manganese (III) acetate complex was prepared in 78% yield from 6,6'-bis(2-hydroxy-3,5-dimethylphenyl)-2,2'-bipyridine using method D; δH [$^2$H$_4$]-MeOH includes: −28, (2H, b), 14.5,(6H, b), 12,(8H, b), −14.5,(2H,b), −19,(2H, b), −42.5,(2H, b); MS 449 (M-OAc)$^+$; HPLC retention time (system 1) 3.35 minutes.

Example 10

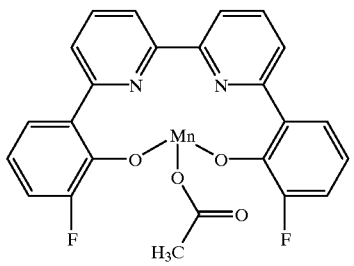

6,6'-Bis(2-hydroxy-3-fluorophenyl)-2,2'-bipyridine (200 mg, 0.53 mmol) and manganese (II) acetate tetrahydrate (130 mg, 0.53 mmol) were mixed in ethanol (10 ml) plus a little water and stirred at room temperature until no ligand remained. The solution was then filtered and reduced to dryness under vacuum to give 6,6'-bis(2-hydroxy-3-fluorophenyl)-2,2'-bipyridine-manganese (III) acetate complex as a brown solid (250 mg, 96%); δH [$^2$H$_4$]-MeOH includes: −25,(2H, b), 11,(2H, b), −8,(2H, b), −11,(2H, b), −21,(2H, b), −43.5,(2H, b); MS 429 (M-OAc)$^+$; HPLC retention time (system 1) 2.56 minutes.

Example 11

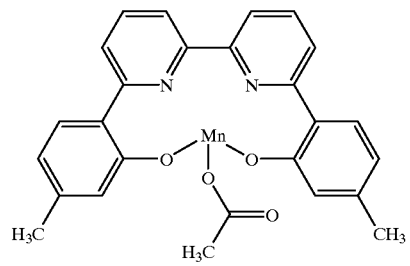

6,6'-Bis(2-hydroxy-4-methylphenyl)-2,2'-bipyridine-manganese (III) acetate complex was prepared in 99% yield from 6,6'-bis(2-hydroxy-4-methylphenyl)-2,2'-bipyridine using method D; δH [$^2$H$_4$]-MeOH includes: −24.5,(2H, b), 12.5,(2H, b), 6,(6H, b), −4,(2H,b), −11.5,(2H, b), −20.5,(2H, b), −43,(2H, b); MS 421 (M-OAc)$^+$; HPLC retention time (system 1) 2.77 minutes.

Example 12

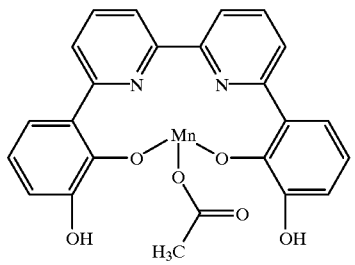

6,6'-Bis(2,3-dihydroxyphenyl)-2,2'-bipyridine (75 mg, 0.20 mmol) and manganese (II) acetate tetrahydrate (54.3 mg, 0.22 mmol) were mixed in ethanol (7 ml) plus water (3 ml) and stirred at room temperature until no ligand remained. The solution was reduced to dryness under vacuum. The brown residue was triturated with acetone to give 6,6'-bis(2,3-dihydroxyphenyl)-2,2'-bipyridine-manganese (III) acetate complex as a brown solid; δH [$^2$H$_4$]-MeOH includes: −24.2,(2H, b), 8.6,(2H, b), −7.3,(2H, b), 19.2,(4H, b), −42.8, (2H, b); MS 425 (M-OAc)$^+$; HPLC retention time (system 1) 2.31 minutes.

Example 13

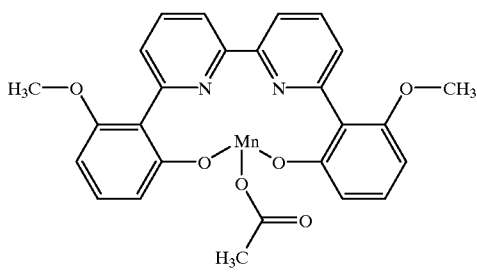

6,6'-Bis(2-hydroxy-6-methoxyphenyl)-2,2'-bipyridine-manganese (III) acetate complex was prepared in 47% yield from 6,6'-bis(2-hydroxy-6-methoxyphenyl)-2,2'-bipyridine using method D; δH [$^2$H$_4$]-MeOH includes: −29.4,(2H, b), 1.2,(2H, b), −2.0,(2H, b), −8.4,(2H, b), −21.8,(2H, b), −41.4, (2H, b); MS 453 (M-OAc)$^+$; retention time (system 1) 2.44 minutes.

Example 14

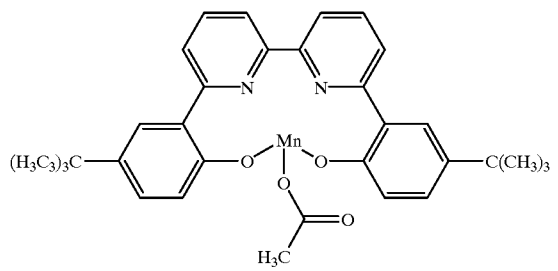

6,6'-Bis(2-hydroxy-5-t-butylphenyl)-2,2'-bipyridine-manganese (III) acetate complex was prepared in 96% yield from 6,6'-bis(2-hydroxy-5-t-butylphenyl)-2,2'-bipyridine using method D; δH [$^2$H$_4$]-MeOH includes: −25.2,(2H, b), 10.8,(2H, b), 1.2,(b), −12.7,(2H, b), −19.1,(2H, b), −42.5, (2H, b); MS 505 (M-OAc)$^+$; HPLC retention time (system 1) 3.09 minutes.

Example 15

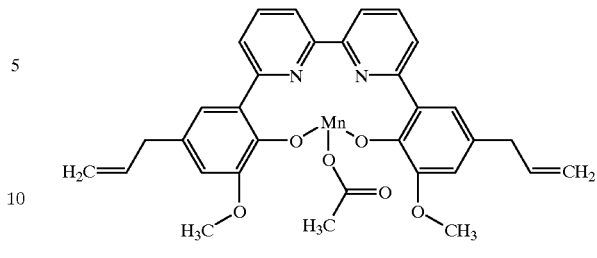

6,6'-Bis(5-allyl-2-hydroxy-3-methoxyphenyl)-2,2'-bipyridine-manganese (III) acetate complex was prepared in 61% yield from 6,6'-bis(5-allyl-2-hydroxy-3-methoxyphenyl)-2,2'-bipyridine using method D; δH [$^2$H$_4$]-MeOH includes: −26.5,(2H, b), 9.9,(b), 5.7,(b), −13.4,(2H, b), −18.9,(2H, b), −42.4,(2H, b); MS 533 (M-OAc)$^-$; HPLC retention time (system 1) 2.73 minutes.

Example 16

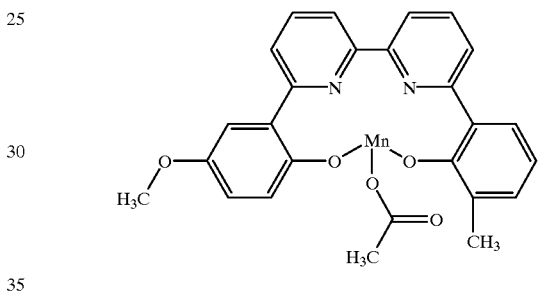

6-(2-Hydroxy-5-methoxyphenyl)-6'-(2-hydroxy-3-methylphenyl)-2,2'-bipyridine-manganese (III) acetate complex was prepared in 81% yield from 6-(2-hydroxy-5-methoxyphenyl)-6'-(2-hydroxy-3-methylphenyl)-2,2'-bipyridine using method D; MS 437 (M-OAc)$^+$; HPLC retention time (system 1) 2.89 minutes.

Example 17

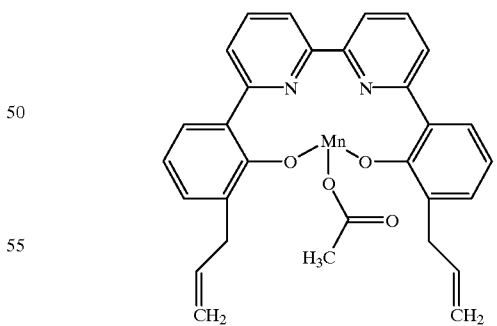

6,6'-Bis(3-allyl-2-hydroxyphenyl)-2,2'-bipyridine-manganese (III) acetate complex was prepared in 51% yield from 6,6'-bis(3-allyl-2-hydroxyphenyl)-2,2'-bipyridine using method D; δH [$^2$H$_4$]-MeOH includes: −25.4,(2H, b), 14.2,(2H, b), −11.3,(2H, b), −16.5,(2H, b), −19.8,(2H, b), −42.5, (2H, b); MS 473 (M-OAc)$^+$; HPLC retention time (system 1) 3.65.

Example 18

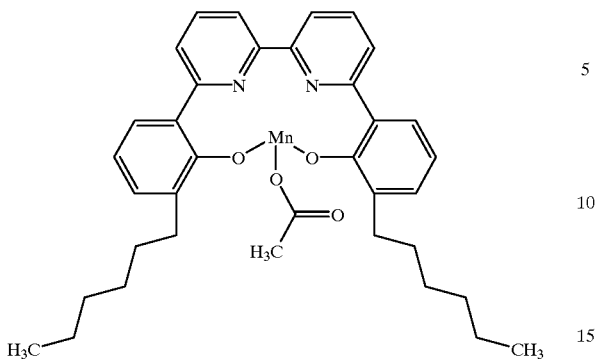

The 6,6'-bis(3-hexyl-2-hydroxyphenyl)-2,2'-bipyridine (80 mg, 0.157 mmol) and manganese (II) acetate tetrahydrate (38.5 mg, 0.157 mmol) were mixed in methanol (30 ml) and stirred at room temperature for 24 hours. The solution was reduced to dryness under vacuum. The residue was triturated with ethyl acetate to give the desired product as a brown solid (67 mg, 69%); δH [$^2$H$_4$]-MeOH includes: −25.8,(2H, b), 14.2,(2H, b), −11.1,(2H, b), −17.1,(2H, b), −19.6,(2H, b), −42.4,(2H, b); MS 620 (MH)$^+$, 561, (M-OAc)$^+$.

Example 19

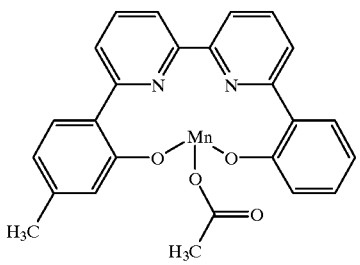

6-(2-Hydroxyphenyl)-6'-(2-hydroxy-4-methylphenyl)-2,2'-bipyridine-manganese (III) acetate complex was prepared in 99% yield from 6-(2-hydroxyphenyl)-6'-(2-hydroxy-4-methylphenyl)-2,2'-bipyridine using method D; MS 407 (M-OAc)$^+$; HPLC retention time (system 1) 2.82 minutes.

Example 20

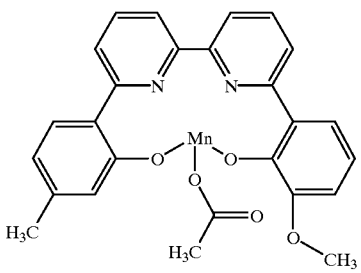

6-(2-Hydroxy-3-methoxyphenyl)-6'-(2-hydroxy-4-methylphenyl)-2,2'-bipyridine-manganese (III) acetate complex was prepared in 81% yield from 6-(2-hydroxy-4-methoxyphenyl)-6'-(2-hydroxy-4-methylphenyl)-2,2'-bipyridine using method D; MS 437 (M-OAc)$^+$; HPLC retention time (system 1) 2.72 minutes.

Example 21

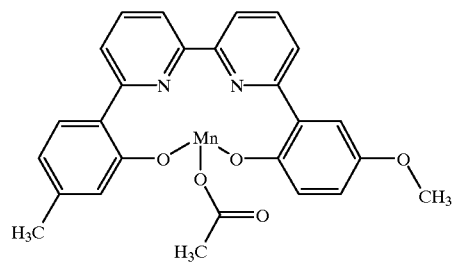

6-(2-Hydroxy-5-methoxyphenyl)-6'-(2-hydroxy-4-methylphenyl)-2,2'-bipyridine-manganese (III) acetate complex was prepared in 65% yield from 6-(2-hydroxy-5-methoxyphenyl)-6'-(2-hydroxy-4-methylphenyl)-2,2'-bipyridine using method D; MS 437 (M-OAc)$^+$; HPLC retention time (system 1) 2.80 minutes.

Example 22

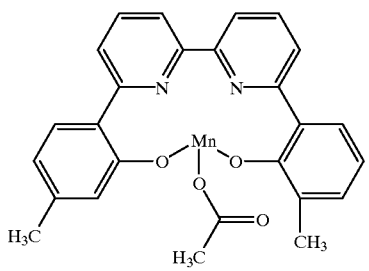

6-(2-Hydroxy-3-methylphenyl)-6'-(2-hydroxy-4-methylphenyl)-2,2'-bipyridine-manganese (III) acetate complex was prepared in 83% yield from 6-(2-hydroxy-3-methylphenyl)-6'-(2-hydroxy-4-methylphenyl)-2,2'-bipyridine using method D; MS 421 (M-OAc)$^+$; HPLC retention time (system 1) 3.19 minutes.

Example 23

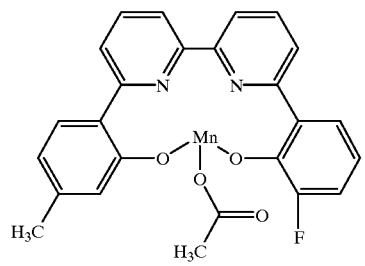

6-(3-Fluoro-2-hydroxyphenyl)-6'-(2-hydroxy-4-methylphenyl)-2,2'-bipyridine-manganese (III) acetate complex was prepared in 54% yield from 6-(3-fluoro-2-hydroxyphenyl)-6'-(2-hydroxy-4-methylphenyl)-2,2'-bipyridine using method D; MS 425 (M-OAc)$^+$; HPLC retention time (system 1) 2.91 minutes.

Example 24

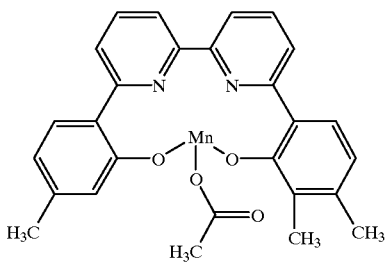

6-(3,4-Dimethyl-2-hydroxyphenyl)-6'-(2-hydroxy-4-methylphenyl)-2,2'-bipyridine-manganese (III) acetate complex was prepared in 81% yield from 6-(3,4-dimethyl-2-hydroxyphenyl)-6'-(2-hydroxy-4-methylphenyl)-2,2'-bipyridine using method D; MS 435 (M-OAc)$^+$; HPLC retention time (system 1) 3.37 minutes.

Example 25

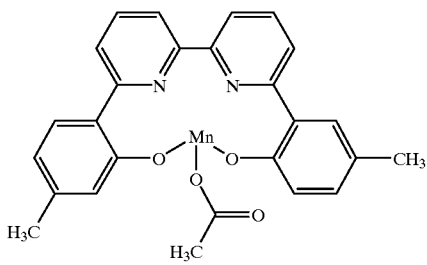

6-(2-Hydroxy-4-methylphenyl)-6'-(2-hydroxy-5-methylphenyl)-2,2'-bipyridine-manganese (III) acetate complex was prepared in 67% yield from 6-(2-hydroxy-4-methylphenyl)-6'-(2-hydroxy-5-methylphenyl)-2,2'-bipyridine using method D; MS 421 (M-OAc)$^+$; HPLC retention time (system 1) 2.94 minutes.

Example 26

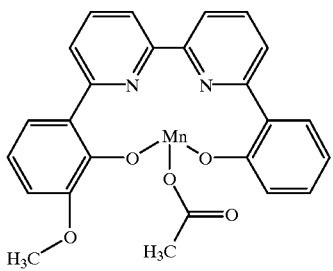

6-(2-Hydroxyphenyl)-6'-(2-hydroxy-3-methoxyphenyl)-2,2'-bipyridine-manganese (III) acetate complex was prepared in 83% yield from 6-(2-hydroxyphenyl)-6'-(2-hydroxy-3-methoxyphenyl)-2,2'-bipyridine using method D; MS 423 (M-OAc)$^+$; HPLC retention time (system 1) 2.56 minutes.

Example 27

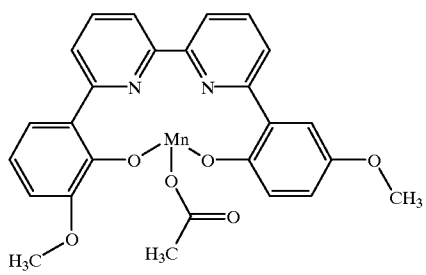

6-(2-Hydroxy-3-methoxyphenyl)-6'-(2-hydroxy-5-methoxyphenyl)-2,2'-bipyridine-manganese (III) acetate complex was prepared in 53% yield from 6-(2-hydroxy-3-methoxyphenyl)-6'-(2-hydroxy-5-methoxyphenyl)-2,2'-bipyridine using method D; MS 453 (M-OAc)$^+$; HPLC retention time (system 1) 2.57 minutes.

Example 28

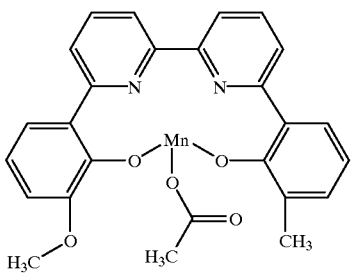

6-(2-Hydroxy-3-methoxyphenyl)-6'-(2-hydroxy-3-methylphenyl)-2,2'-bipyridine-manganese (III) acetate complex was prepared in 65% yield from 6-(2-hydroxy-3-methoxyphenyl)-6'-(2-hydroxy-3-methylphenyl)-2,2'-bipyridine using method D; MS 437 (M-OAc)$^+$; HPLC retention time (system 1) 2.80 minutes.

Example 29

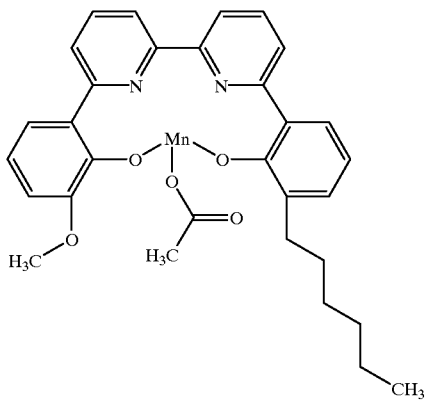

6-(2-Hydroxy-3-hexylphenyl)-6'-(2-hydroxy-3-methoxyphenyl)-2,2'-bipyridine manganese (III) acetate complex was prepared in 71% yield from 6-(2-hydroxy-3-hexylphenyl)-6'-(2-hydroxy-3-methoxyphenyl)-2,2'-bipyridine using method D; MS 507 (M-OAc)$^+$; HPLC retention time (system 1) 3.76 minutes.

Example 30

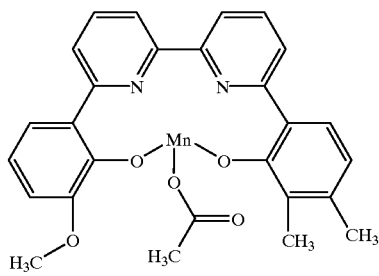

6-(3,4-Dimethyl-2-hydroxyphenyl)-6'-(2-hydroxy-3-methoxyphenyl)-2,2'-bipyridine-manganese (III) acetate complex was prepared in 76% yield from 6-(3,4-dimethyl-2-hydroxyphenyl)-6'-(2-hydroxy-3-methoxyphenyl)-2,2'-bipyridine using method D; MS 451 (M-OAc)$^+$; HPLC retention time (system 1) 3.01 minutes.

Example 31

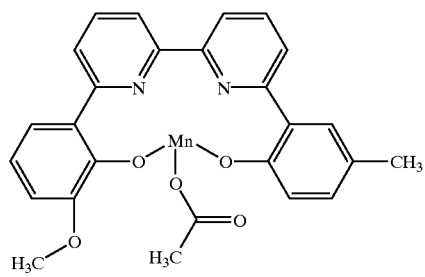

6-(2-Hydroxy-3-methoxyphenyl)-6'-(2-hydroxy-5-methylphenyl)-2,2'-bipyridine-manganese (III) acetate complex was prepared in 97% yield from 6-(2-Hydroxy-3-methoxyphenyl)-6'-(2-hydroxy-5-methylphenyl)-2,2'-bipyridine using method D; MS 437 (M-OAc)$^+$; HPLC retention time (system 1) 2.69 minutes.

Example 32

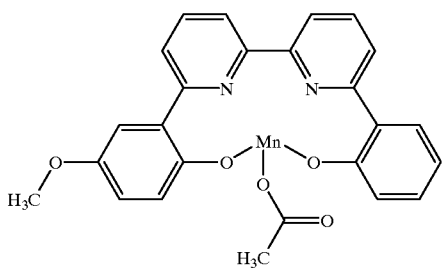

6-(2-Hydroxyphenyl)-6'-(2-hydroxy-5-methoxyphenyl)-2,2'-bipyridine-manganese (III) acetate complex was prepared in 87% yield from 6-(2-hydroxyphenyl)-6'-(2-hydroxy-5-methoxyphenyl)-2,2'-bipyridine using method D; MS 423 (M-OAc)$^+$; HPLC retention time (system 1) 2.61 minutes.

Example 33

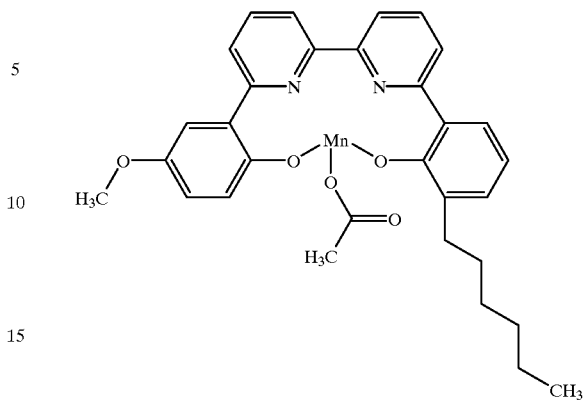

6-(3-Hexyl-2-hydroxyphenyl)-6'-(2-hydroxy-5-methoxyphenyl)-2,2'-bipyridine-manganese (III) acetate complex was prepared in 69% yield from 6-(3-hexyl-2-hydroxyphenyl)-6'-(2-hydroxy-5-methoxyphenyl)-2,2'-bipyridine using method D; MS 507 (M-OAc)$^+$; HPLC retention time (system 1) 3.89 minutes.

Example 34

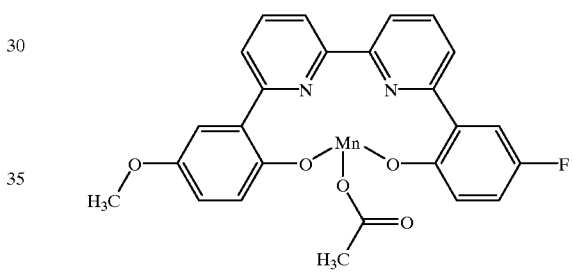

6-(5-Fluoro-2-hydroxyphenyl)-6'-(2-hydroxy-5-methoxyphenyl)-2,2'-bipyridine-manganese (III) acetate complex was prepared in 76% yield from 6-(5-fluoro-2-hydroxyphenyl)-6'-(2-hydroxy-5-methoxyphenyl)-2,2'-bipyridine using method D; MS 441 (M-OAc)$^+$; HPLC retention time (system 1) 2.63 minutes.

Example 35

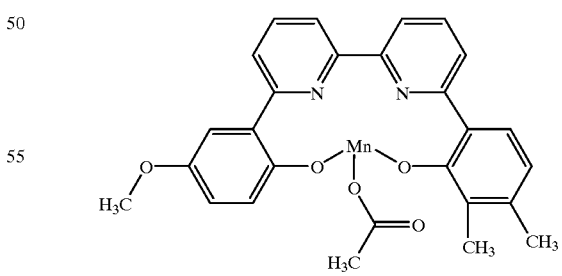

6-(3,4-Dimethyl-2-hydroxyphenyl)-6'-(2-hydroxy-5-methoxyphenyl)-2,2'-bipyridine-manganese (III) acetate complex was prepared in 75% yield from 6-(3,4-dimethyl-2-hydroxyphenyl)-6'-(2-hydroxy-5-methoxyphenyl)-2,2'-bipyridine using method D; MS 451 (M-OAc)$^+$; HPLC retention time (system 1) 3.06 minutes.

Example 36

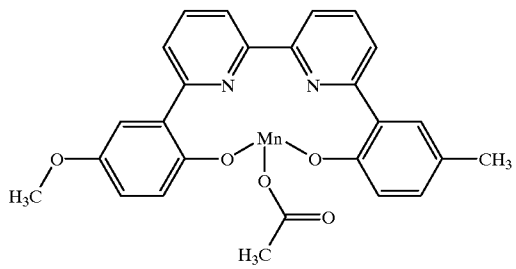

6-(2-Hydroxy-5-methoxyphenyl)-6'-(2-hydroxy-5-methylphenyl)-2,2'-bipyridine-manganese (III) acetate complex was prepared in 93% yield from 6-(2-hydroxy-5-methoxyphenyl)-6'-(2-hydroxy-5-methylphenyl)-2,2'-bipyridine using method D; MS 437 (M-OAc)$^+$; HPLC retention time (system 1) 2.73 minutes.

Example 37

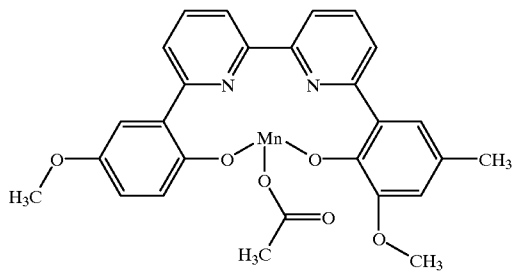

6-(2-Hydroxy-5-methoxyphenyl)-6'-(2-hydroxy-3-methoxy-5-methylphenyl)-2,2'-bipyridine-manganese (III) acetate complex was prepared in 91% yield from 6-(2-hydroxy-5-methoxyphenyl)-6'-(2-hydroxy-3-methoxy-5-methylphenyl)-2,2'-bipyridine using method D; MS 467 (M-OAc)$^+$; HPLC retention time (system 1) 2.65 minutes.

Example 38

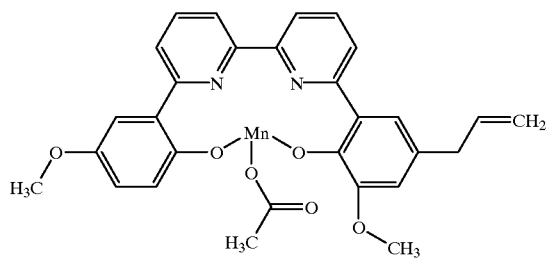

6-(2-Hydroxy-5-methoxyphenyl)-6'-(5-allyl-2-hydroxy-3-methoxyphenyl)-2,2'-bipyridine-manganese (III) acetate complex was prepared in 83% yield from 6-(2-hydroxy-5-methoxyphenyl)-6'-(5-allyl-2-hydroxy-3-methoxyphenyl)-2,2'-bipyridine using method D; MS 493 (M-OAc)$^+$; HPLC retention time (system 1) 2.77 minutes.

Example 39

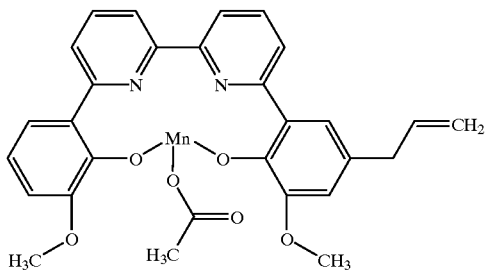

6-(2-Hydroxy-3-methoxyphenyl)-6'-(5-allyl-2-hydroxy-3-methoxyphenyl)-2,2'-bipyridine-manganese (III) acetate complex was prepared in 80% yield from 6-(2-hydroxy-3-methoxyphenyl)-6'-(5-allyl-2-hydroxy-3-methoxyphenyl)-2,2'-bipyridine using method D; MS 493 (M-OAc)$^+$; HPLC retention time (system 1) 2.78 minutes.

Example 40

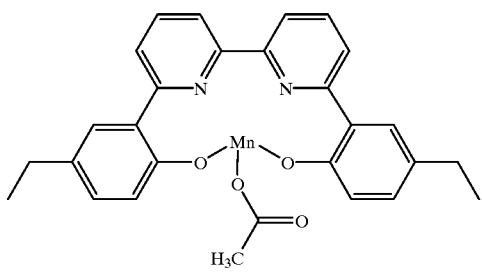

6,6'-Bis(5-ethyl-2-hydroxyphenyl)-2,2'-bipyridine-manganese (III) acetate complex was prepared in 81% yield from 6,6'-bis(5-ethyl-2-hydroxyphenyl)-2,2'-bipyridine using method D; MS 449 (M-OAc)$^+$; HPLC retention time (system 1) 3.07 minutes.

Example 41

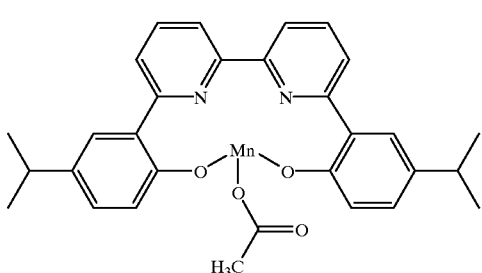

6,6'-Bis(2-hydroxy-5-isopropylphenyl)-2,2'-bipyridine-manganese (III) acetate complex was prepared in 47% yield from 6,6'-bis(2-hydroxy-5-isopropylphenyl)-2,2'-bipyridine using method D; MS 477 (M-OAc)$^+$; HPLC retention time (system 1) 3.17 minutes.

Example 42

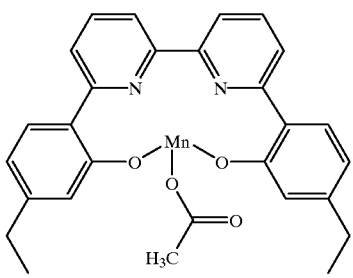

6,6'-Bis(4-ethyl-2-hydroxyphenyl)-2,2'-bipyridine-manganese (III) acetate complex was prepared in 21% yield from 6,6'-bis(4-ethyl-2-hydroxyphenyl)-2,2'-bipyridine using method D; MS 449 (M-OAc)$^+$; HPLC retention time (system 1) 3.26 minutes.

Example 43

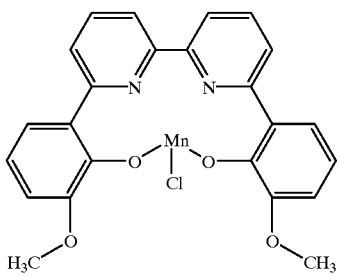

6,6'-Bis(2-hydroxy-3-methoxyphenyl)-2,2'-bipyridine-manganese (III) chloride was prepared from 6,6'-Bis(2-hydroxy-3-methoxyphenyl)-2,2'-bipyridine-manganese (III) acetate complex (Example 3) using method G. MS 488 M$^+$, 453 (M-Cl)$^+$. HPLC retention time (system 1) 2.28 minutes.

Examples 44 to 84

The chloride complexes corresponding to Examples 1, 2 and 4 to 42 are prepared in an analogous way to Example 43.

BIOLOGICAL DATA

Compounds of the present invention were tested for antioxidant catalytic activity in suitable SOD, CAT and POD assays as detailed below.

I. Superoxide Dismutase (SOD) Assay

This method is adapted from what has become the standard method for the measurement of SOD activity (McCord J. M., Fridovich, I., *J. Biol. Chem.* 244, 6049–6055, 1969). Briefly, a steady-state production of superoxide anion was maintained by the action of xanthene oxidase (XO) on hypoxanthene (HX) at physiological pH. Presence of the anion was measured by the reduction of XTT (3'-{1-(phenylamino)-carbonyl]-3,4-tetrazolium]-bis(4-methoxy-6-nitro)benzsulphonic acid to a water-soluble product with an absorbance maximum at ~470 nm. Hypoxanthene concentrations were titrated so as to give a steady-state rate of XTT reduction of 0.025 Optical Density Units (OD) per minute at 25° C.

The assays for compound antioxidant activity were carried out in 96-well microtitre plates using a DIAS modular assay robot instrument (Dynatech Ltd.) Compounds were solublised in DMF at 10 mM. DMF concentrations in the assay never exceeded 1%, were tolerated and were controlled for in assay plates.

Xanthene oxidase (Sigma X1875) 0.01 U/ml and XTT (Sigma X4251), 0.5 mM and hypoxanthene (Sigma H9377), typically at 100 mM, were incubated in the presence of various doses of compounds at 25° C. in 0.05M Tris/HCl pH 7.4. Rates of XTT reduction were measured over 5 minutes at 490 nm. Dose-response curves were constructed for inhibition by the compound of control rates of XTT reduction. IC$_{50}$ concentrations were derived using a four-parameter logistic model using the software tools Excel (Microsoft Corp.) and Xlfit (ID Business Solutions). This concentration is equivalent to one International Unit of SOD activity. These values were normalised to units of U/mmol compound.

II. Catalase (CAT) Assay

This method measures catalase activity as the ability to remove hydrogen peroxide from solution in the absence of hydrogen donors over one hour. After this time any remaining peroxide was removed by introduction to the mixture of high concentrations of horseradish peroxidase and the hydrogen donor 2,2'-azino-di-[3-ethyl-benzothiazoline-(6)-sulphonic acid (ABTS). This rapid reaction produces peroxide-concentration-dependant product with a maximal absorbance at 405 nm.

The assays for compound antioxidant activity were carried out in 96-well microtitre plates using a DIAS modular assay robot instrument (Dynatech Ltd.) Compounds were solublised in DMF at 10 mM. DMF concentrations in the assay never exceeded 1%, were tolerated and were controlled for in assay plates.

Hydrogen peroxide (Sigma H1009) 10 mM was incubated with various concentrations of compound in 0.05M Tris HCl pH 7.4 at 25° C. for 60 mins. In addition, a standard range of concentrations of hydrogen peroxide were placed on every microtitre plate. After incubation 0.1 volumes of a mixture of horseradish peroxidase (Sigma P-6140) 1U/ml and ABTS (Sigma A-1888) 3 mM was added. The resultant reaction was allowed to go to completion by incubation at 25° C. for 60 mins. Plates were then read for absorbance at 405 nm. A standard curve for absorbance against known hydrogen peroxide concentration was constructed. Absorbance data for wells containing compound were interpolated against this curve using the software tools Excel (Microsoft Corp.) and Xlfit (ID Business Solutions). This analysis gives the amount of hydrogen peroxide removed per minute, per mmol of compound.

III. Peroxidase (POD) Assay

This method measures the ability of the compounds to remove hydrogen peroxide in the presence of the hydrogen donor 2,2'-azino-di-[3-ethyl-benzothiazoline-(6)-sulphonic acid (ABTS) (Galati, H., *J. Clin. Chem. Clin. Biochem.* (1979) 17, 1–7).

The assays for compound antioxidant activity were carried out in 96-well microtitre plates using a DIAS modular assay robot instrument (Dynatech Ltd.) Compounds were solublised in DMF at 10 mM. DMF concentrations in the assay never exceeded 1%, were tolerated and were controlled for in assay plates.

ABTS (Sigma A-1888) 3 mM was incubated with various concentrations of compound in 0.05M Tris HCl pH 7.4 at 25° C. A range of standard concentrations of horseradish peroxidase (Sigma P-6140) were included on each microtitre plate. Hydrogen peroxide (Sigma H1009) 100 mM was added and the plate incubated at 25° C. for 2 minutes. Absorbance at 405 nm was measured and the rates of ABTS reduction calculated. A standard curve was constructed using data from wells containing known concentrations of peroxidase. Data for wells containing compound were interpolated against this curve using the software tools Excel (Microsoft Corp.) and Xlfit (ID Business Solutions). Estimations of peroxidase activity were given as International Units of peroxidase activity/mmol compound.

The results of testing the compounds of the Examples in the assays described above are given in Table 1 below.

TABLE 1

Results of Bipyridine Manganese Complexes in SOD, CAT and POD assays

|  | SOD | CAT | POD |
|---|---|---|---|
| Example 1 | 215.35 | 0.126 | 8209.22 |
| Example 2 | 137.3 | 0.195 | 6000 |
| Example 3 | 203.5 | 0.132 | 583.5 |
| Example 4 | 205.52 | 0.127 | 2100.905 |
| Example 5 | 211.15 | 0.235 | 4336.81 |
| Example 6 | 208.95 | 0.078 | 8269.1 |
| Example 7 | 188.6 | 0.008 | 3916.31 |
| Example 8 | 101 | 0.072 | 4560.19 |
| Example 9 | 249.45 | 0.072 | 1772.035 |
| Example 10 | 255.3 | 0.07 | 1327.355 |
| Example 11 | 162.7 | 0.199 | 6067.78 |
| Example 12 | 234.75 | 0.053 | 324.855 |
| Example 13 | 155 | 0.082 | 18222.5 |
| Example 14 | 140 | 0.1475 | 12709.5 |
| Example 15 | 145.4 | 0.206 | |
| Example 16 | 97 | 0.4595 | 44217 |
| Example 18 | 41.43 | 0.0083 | 209.92 |
| Example 19 | 86 | 0.0885 | |
| Example 20 | 183.5 | 0.303 | |
| Example 21 | 129.5 | 0.4025 | 422177 |
| Example 22 | 177 | 0.09 | 4524587 |
| Example 23 | 122.5 | 0.0765 | 711049 |
| Example 24 | 149 | 0.1145 | 427224 |
| Example 25 | 116 | 0.1805 | |
| Example 26 | 137.5 | 0.277 | 1247939 |
| Example 27 | 124 | 0.3135 | |
| Example 28 | 182.5 | 0.176 | |
| Example 29 | 140.5 | 0.0615 | |
| Example 30 | 145 | 0.1085 | 419624 |
| Example 31 | 142.5 | 0.2695 | 772740 |
| Example 32 | 159 | 0.488 | |
| Example 33 | 133.5 | 0.1035 | |
| Example 34 | 162 | 0.489 | 60324.5 |
| Example 35 | 258.5 | 0.672 | |
| Example 36 | 193 | 0.6345 | 687026 |
| Example 37 | 173 | 0.398 | |
| Example 38 | 187 | 0.2815 | 490484 |
| Example 39 | 179 | 0.265 | 205101 |

The catalase assay procedure described above provides certain advantages over previously described assays. Prior art assays of catalase activity involve direct measurement either of the amount of oxygen produced (generally using an oxygen electrode) or of the amount of hydrogen peroxide remaining (by UV absorption which generally involves use of a quartz vessel). The assay described above instead employs an indirect measurement of hydrogen peroxide concentration. The addition of peroxidase and ABTS after an appropriate time period results in immediate oxidation by POD of the ABTS using the remaining hydrogen peroxide. The oxidation of ABTS results in a colour change which can be measured. This allows the assay to be performed in a format which is simpler and which also provides for increased compound throughput relative to previous techniques. For example, the the assay can be run in a multi-well plate format (such as a 96-well plate format).

IV. In Vivo Data: Middle Cerebral Artery Occlusion Model (MCA-o)

A middle cerebral artery occlusion (MCA-o) surgical procedure was performed on 250–300 g male Sprague-Dawley rats. Rats were anesthetized with an intraperitoneal injection of 3–5 mL/kg of 10% chloral hydrate. The left MCA was located by making a 1.0 cm horizontal incision in the upper left temporal region from the lateral canthus of the eye to the external auditory canal. A vertical 1.0 cm incision was then made about 3.0 mm from the auditory canal. This resulted in horizontal bisection of the temporalis muscle and vertical bisection of the masseter muscle. The muscles were reflected to expose the skull between the frontal and parietal bones above the zygomatic arch. A 3.0 mm diameter opening was made to expose the MCA. The MCA was permanently occluded well below the bifurcation using cauterization. After surgery, rats were placed under a heating lamp to maintain body temperature, which was monitored rectally. Rats received a bolus tail vein injection of a compound in 0.9% sterile saline vehicle or vehicle as control either immediately before surgery or 3 hours post surgery. Animals were assigned to a treatment group in a randomized fashion as necessary either before or after completion of surgery; the investigator performing the surgery was unaware of the treatment. Rats were sacrificed by cervical dislocation and immediate decapitation 24 hours after surgery for analysis of brain infarct volumes. To visualize infarcted and uninfarcted tissue, the brains were removed and sectioned coronally into ten 0.5 mm slices. These sections were stained with 2.5% 2,3,5-triphenyltetrazolium chloride (TTC) and preserved with 4% formalin. Infarcted and uninfarcted tissue sections for each brain were quantitated by image analysis.

Table 2 lists the percentage of neuroprotection when the compound of Example 1 was administered immediately before surgery or 3 hours after surgery as compared to the control. The number of animals for each group varied from between 8 and 10.

TABLE 2

| Dose of Compound (mg/kg iv) | Time of Administration | % Neuroprotection |
|---|---|---|
| 1 | Immediately before surgery | 66.4 |
| 1 | 3 hours post surgery | 64.0 |
| CONTROL | BEFORE AND AFTER | 0 |

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Structural Formula (I):

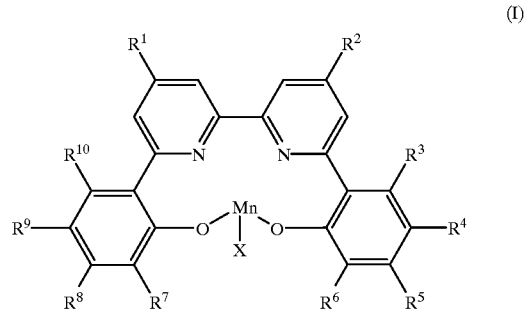

and solvates thereof, wherein:

X represents a counter-anion;

R$^1$ and R$^2$ each, independently, represent hydrogen, C$_{1-6}$ alkoxy or nitro;

R$^3$–R$^{10}$ each, independently, represents hydrogen, hydroxy, halo, C$_{1-6}$ alkyl, C$_{2-6}$ alkenyl or C$_{1-6}$ alkoxy.

2. The compound of claim 1, wherein R$^1$ and R$^2$ each, independently, are selected from the group consisting of hydrogen, methoxy and ethoxy.

3. The compound of claim 1, wherein R$^1$ and R$^2$ are the same.

4. The compound of claim 2, wherein R$^1$ and R$^2$ are hydrogen.

5. The compound of claim 1, wherein R$^3$ to R$^{10}$ are each, independently, selected from the group consisting of hydrogen, hydroxy, fluoro, methyl, ethyl, isopropyl, tert-butyl, n-hexyl, propenyl, methoxy and ethoxy.

6. The compound of claim 5, wherein R$^3$ is hydrogen or methoxy.

7. The compound of claim 5, wherein R$^5$, and R$^8$ are each, independently, hydrogen, methyl or ethyl.

8. The compound of claim 5, wherein R$^{10}$ is hydrogen or methoxy.

9. The compound of claim 1, wherein the phenyl carrying groups R$^3$ to R$^6$ is substituted identically to the phenyl ring carrying the groups R$^7$ to R$^{10}$.

10. The compound of claim 1, wherein X is acetate or chloride.

11. The compound of claim 1, wherein:

R$^1$, R$^2$, R$^3$, R$^8$ and R$^{10}$ are each hydrogen;

R$^4$ and R$^9$ are each, independently, hydrogen or methoxy;

R$^5$ is hydrogen or methyl;

R$^6$ and R$^7$ are each, independently, hydrogen, methyl and methoxy; and

X is acetate or chloride.

12. The compound of claim 1 selected from the group consisting of:

6,6'-Bis(2-hydroxyphenyl)-2,2'-bipyridine-manganese (III) acetate or chloride;

6,6'-Bis(2-hydroxy-5-methoxyphenyl)-2,2'-bipyridine-manganese (III) acetate or chloride;

6,6'-Bis(2-hydroxy-3-methoxyphenyl)-2,2'-bipyridine-manganese (III) acetate or chloride;

6,6'-Bis(2-hydroxy-3-ethoxyphenyl)-2,2'-bipyridine-manganese (III) acetate or chloride;

6,6'-Bis(2-hydroxy-3-methoxy-5-methylphenyl)-2,2'-bipyridine-manganese (III) acetate or chloride;

6,6'-Bis(2-hydroxy-5-fluorophenyl)-2,2'-bipyridine-manganese (III) acetate or chloride;

6,6'-Bis(2-hydroxy-5-methylphenyl)-2,2'-bipyridine-manganese (III) acetate or chloride;

6,6'-Bis(2-hydroxy-3-methylphenyl)-2,2'-bipyridine-manganese (III) acetate or chloride;

6,6'-Bis(2-hydroxy-3,5-dimethylphenyl)-2,2'-bipyridine-manganese (III) acetate or chloride;

6,6'-Bis(2-hydroxy-3-fluorophenyl)-2,2'-bipyridine-manganese (III) acetate or chloride;

6,6'-Bis(2-hydroxy-4-methylphenyl)-2,2'-bipyridine-manganese (III) acetate or chloride;

6,6'-Bis(2,3-dihydroxyphenyl)-2,2'-bipyridine-manganese (III) acetate or chloride;

6,6'-Bis(2-hydroxy-6-methoxyphenyl)-2,2'-bipyridine-manganese (III) acetate or chloride;

6,6'-Bis(2-hydroxy-5-t-butylphenyl)-2,2'-bipyridine-manganese (III) acetate or chloride;

6,6'-Bis(5-allyl-2-hydroxy-3-methoxyphenyl)-2,2'-bipyridine-manganese (III) acetate or chloride;

6-(2-Hydroxy-5-methoxyphenyl)-6'-(2-hydroxy-3-methylphenyl)-2,2'-bipyridine-manganese (III) acetate or chloride;

6,6'-Bis(3-allyl-2-hydroxyphenyl)-2,2'-bipyridine-manganese (III) acetate or chloride;

6,6'-Bis(3-hexyl-2-hydroxyphenyl)-2,2'-bipyridine-manganese (III) acetate or chloride;

6-(2-Hydroxyphenyl)-6'-(2-hydroxy-4-methylphenyl)-2,2'-bipyridine-manganese (III) acetate or chloride;

6-(2-Hydroxy-3-methoxyphenyl)-6'-(2-hydroxy-4-methylphenyl)-2,2'-bipyridine-manganese (III) acetate or chloride;

6-(2-Hydroxy-5-methoxyphenyl)-6'-(2-hydroxy-4-methylphenyl)-2,2'-bipyridine-manganese (III) acetate or chloride;

6-(2-Hydroxy-3-methylphenyl)-6'-(2-hydroxy-4-methylphenyl)-2,2'-bipyridine-manganese (III) acetate or chloride;

6-(3-Fluoro-2-hydroxyphenyl)-6'-(2-hydroxy-4-methylphenyl)-2,2'-bipyridine-manganese (III) acetate or chloride;

6-(3,4-Dimethyl-2-hydroxyphenyl)-6'-(2-hydroxy-4-methylphenyl)-2,2'-bipyridine-manganese (III) acetate or chloride;

6-(2-Hydroxy-4-methylphenyl)-6'-(2-hydroxy-5-methylphenyl)-2,2'-bipyridine-manganese (III) acetate or chloride;

6-(2-Hydroxyphenyl)-6'-(2-hydroxy-3-methoxyphenyl)-2,2'-bipyridine-manganese (III) acetate or chloride;

6-(2-Hydroxy-3-methoxyphenyl)-6'-(2-hydroxy-5-methoxyphenyl)-2,2'-bipyridine-manganese (III) acetate or chloride;

6-(2-Hydroxy-3-methoxyphenyl)-6'-(2-hydroxy-3-methylphenyl)-2,2'-bipyridine-manganese (III) acetate or chloride;

6-(2-Hydroxy-3-hexylphenyl)-6'-(2-hydroxy-3-methoxyphenyl)-2,2'-bipyridine-manganese (III) acetate or chloride;

6-(3,4-Dimethyl-2-hydroxyphenyl)-6'-(2-hydroxy-3-methoxyphenyl)-2,2'-bipyridine-manganese (III) acetate or chloride;

6-(2-Hydroxy-3-methoxyphenyl)-6'-(2-hydroxy-5-methylphenyl)-2,2'-bipyridine-manganese (III) acetate;

6-(2-Hydroxyphenyl)-6'-(2-hydroxy-5-methoxyphenyl)-2,2'-bipyridine-manganese (III) acetate or chloride;

6-(3-Hexyl-2-hydroxyphenyl)-6'-(2-hydroxy-5-methoxyphenyl)-2,2'-bipyridine-manganese (III) acetate or chloride;

6-(5-Fluoro-2-hydroxyphenyl)-6'-(2-hydroxy-5-methoxyphenyl)-2,2'-bipyridine-manganese (III) acetate or chloride;

6-(3,4-Dimethyl-2-hydroxyphenyl)-6'-(2-hydroxy-5-methoxyphenyl)-2,2'-bipyridine-manganese (III) acetate or chloride;

6-(2-Hydroxy-5-methoxyphenyl)-6'-(2-hydroxy-5-methylphenyl)-2,2'-bipyridine-manganese (III) acetate or chloride;

6-(2-Hydroxy-5-methoxyphenyl)-6'-(2-hydroxy-3-methoxy-5-methylphenyl)-2,2'-bipyridine-manganese (III) acetate or chloride;

6-(2-Hydroxy-5-methoxyphenyl)-6'-(5-allyl-2-hydroxy-3-methoxyphenyl)-2,2'-bipyridine-manganese (III) acetate or chloride;

6-(2-Hydroxy-3-methoxyphenyl)-6'-(5-allyl-2-hydroxy-3-methoxyphenyl)-2,2'-bipyridine-manganese (III) acetate or chloride;

6,6'-Bis(5-ethyl-2-hydroxyphenyl)-2,2'-bipyridine-manganese (III) acetate or chloride;

6,6'-Bis(2-hydroxy-5-isopropylphenyl)-2,2'-bipyridine-manganese (III) acetate or chloride; and 6,6'-Bis(4-ethyl-2-hydroxyphenyl)-2,2'-bipyridine-manganese (III) acetate or chloride.

13. The compound of claim 1 selected from the group consisting of:

6,6'-Bis(2-hydroxyphenyl)-2,2'-bipyridine-manganese (III) acetate or chloride;

6,6'-Bis(2-hydroxy-5-methoxyphenyl)-2,2'-bipyridine-manganese (III) acetate or chloride;

6,6'-Bis(2-hydroxy-3-methoxyphenyl)-2,2'-bipyridine-manganese (III) acetate or chloride;

6,6'-Bis(2-hydroxy-3-methylphenyl)-2,2'-bipyridine-manganese (III) acetate or chloride;

6-(3,4-Dimethyl-2-hydroxyphenyl)-6'-(2-hydroxy-5-methoxyphenyl)-2,2'-bipyridine-manganese (III) acetate or chloride;

6-(2-Hydroxy-5-methoxyphenyl)-6'-(2-hydroxy-5-methylphenyl)-2,2'-bipyridine-manganese (III) acetate or chloride; and solvates thereof.

14. A compound represented by the following structural formula:

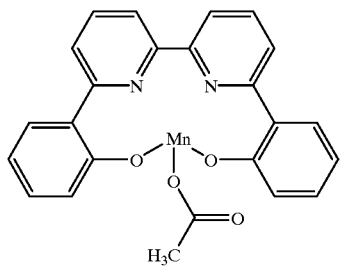

15. A compound represented by the following structural formula:

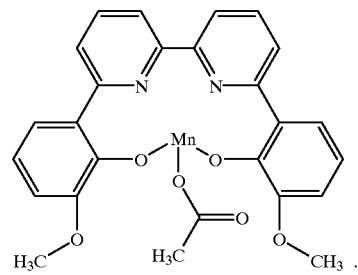

16. A method of preparing a compound represented by Structural Formula (I):

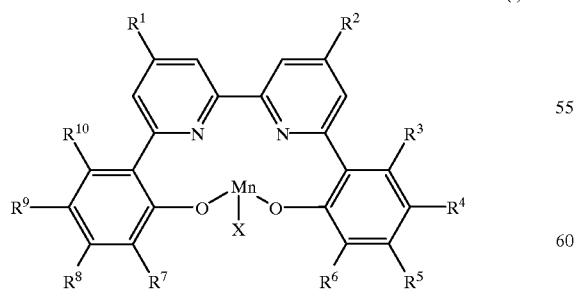

(I)

and solvates thereof, wherein:

X represents a counter-anion;

$R^1$ and $R^2$ each, independently, represents hydrogen, $C_{1-6}$ alkoxy or nitro;

$R^3$, $R^4$, $R^5$ and $R^6$ each, independently, represents hydrogen, hydroxy, halo, $C_{1-6}$ alkyl, $C_{2-6}$ alkenyl or $C_{1-6}$ alkoxy; and $R^7$, $R^8$, $R^9$ and $R^{10}$ each, independently, represents hydrogen, hydroxy, halo, $C_{1-6}$ alkyl, $C_{2-6}$ alkenyl or $C_{1-6}$ alkoxy, comprising the steps of:

a) reacting a bipyridine derivative represented by Structural Formula (III):

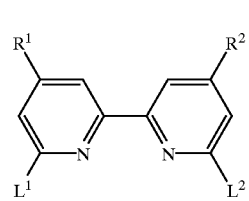

(III)

wherein $L^1$ and $L^2$ are each, independently, a leaving group, with a first boronic acid derivative represented by Structural Formula (IV):

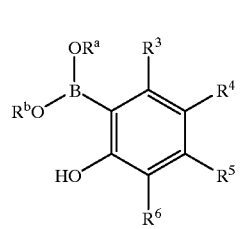

(IV)

wherein $R^a$ and $R^b$ are each, independently, hydrogen or a $C_{1-6}$ alkyl, or $R^a$ and $R^b$ together form a straight-chain or branched alkylene, to form a first intermediate represented by Structural Formula (VI):

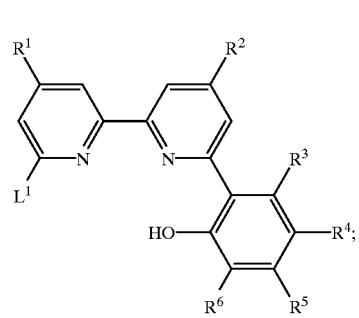

(VI)

b) reacting the first intermediate with a second boronic acid derivative represented by Structural Formula (VII):

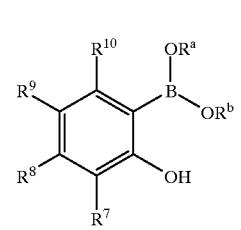

(VII)

to form a second intermediate represented by Structural Formula (II):

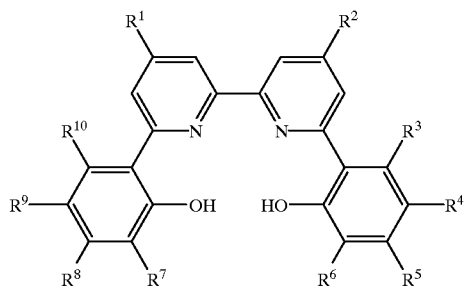

(II)

c) contacting the second intermediate with a manganese(II) salt, thereby forming said compound.

17. The method of claim 16, wherein X is acetate.

18. The method of claim 17, further comprising contacting said compound with a chloride salt, thereby forming said compound wherein X is chloride.

19. The method of claim 16, wherein $L^1$ and $L^2$ are bromine.

20. A pharmaceutical formulation comprising one or more pharmaceutically acceptable carriers, diluents or excipients and a therapeutically effective amount of at least one compound represented by Structural Formula (I):

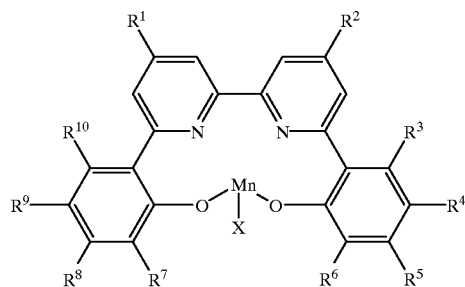

(I)

and solvates thereof, wherein:
X represents a counter-anion;
$R^1$ and $R^2$ each, independently, represents hydrogen, $C_{1-6}$ alkoxy or nitro;
$R^3$, $R^4$, $R^5$ and $R^6$ each, independently, represents hydrogen, hydroxy, halo, $C_{1-6}$ alkyl, $C_{2-6}$ alkenyl or $C_{1-6}$ alkoxy; and
$R^7$, $R^8$, $R^9$ and $R^{10}$ each, independently, represents hydrogen, hydroxy, halo, $C_{1-6}$ alkyl, $C_{2-6}$ alkenyl or $C_{1-6}$ alkoxy.

21. A compound represented by Structural Formula (Ia):

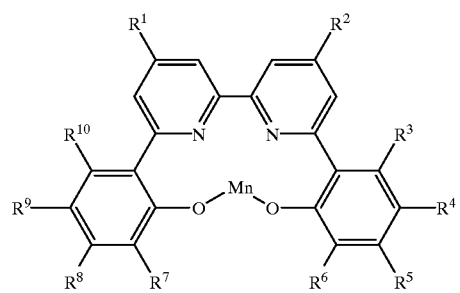

(Ia)

and solvates thereof, wherein:
$R^1$ and $R^2$ each, independently, represent hydrogen, $C_{1-6}$ alkoxy or nitro;
$R^3$, $R^4$, $R^5$ and $R^6$ each, independently, represents hydrogen, hydroxy, halo, $C_{1-6}$ alkyl, $C_{2-6}$ alkenyl or $C_{1-6}$ alkoxy; and
$R^7$, $R^8$, $R^9$ and $R^{10}$ each, independently, represents hydrogen, hydroxy, halo, $C_{1-6}$ alkyl, $C_{2-6}$ alkenyl or $C_{1-6}$ alkoxy.

22. A compound represented by Structural Formula (II):

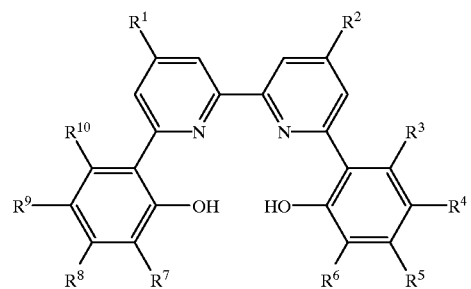

(II)

and solvates thereof, wherein:
$R^1$ and $R^2$ each, independently, represent hydrogen, $C_{1-6}$ alkoxy or nitro;
$R^3$, $R^4$, $R^5$ and $R^6$ each, independently, represents hydrogen, hydroxy, halo, $C_{1-6}$ alkyl, $C_{2-6}$ alkenyl or $C_{1-6}$ alkoxy; and
$R^7$, $R^8$, $R^9$ and $R^{10}$ each, independently, represents hydrogen, hydroxy, halo, $C_{1-6}$ alkyl, $C_{2-6}$ alkenyl or $C_{1-6}$ alkoxy, provided that $R^1$–$R^{10}$ are not all hydrogen.

* * * * *